US010773057B1

(12) United States Patent
LeLievre et al.

(10) Patent No.: US 10,773,057 B1
(45) Date of Patent: Sep. 15, 2020

(54) MEDICAL APPLIANCE SECUREMENT DEVICE

(71) Applicant: M.C. Johnson Company, Inc., Fort Myers, FL (US)

(72) Inventors: Matthew John LeLievre, Estero, FL (US); David E. Dewitt, Lenior City, TN (US); Tracey E. Herald, Knoxville, TN (US)

(73) Assignee: M.C. JOHNSON COMPANY, INC., Fort Myers, FL (US)

( * ) Notice: Subject to any disclaimer, the term of this patent is extended or adjusted under 35 U.S.C. 154(b) by 294 days.

(21) Appl. No.: 15/435,239

(22) Filed: Feb. 16, 2017

Related U.S. Application Data

(60) Provisional application No. 62/295,972, filed on Feb. 16, 2016.

(51) Int. Cl.
  *A61M 5/32* (2006.01)
  *A61M 25/02* (2006.01)
  *A61M 27/00* (2006.01)

(52) U.S. Cl.
  CPC ............ *A61M 25/02* (2013.01); *A61M 27/00* (2013.01); *A61M 2025/0266* (2013.01)

(58) Field of Classification Search
  CPC ...... A61M 16/0683; A61M 2005/1416; A61M 2025/028; A61M 5/158; A61M 25/02; A61M 2025/0253; A61M 2025/026; A61M 2025/0265; A61M 2025/0266; A61M 2025/0273
  See application file for complete search history.

(56) References Cited

U.S. PATENT DOCUMENTS

| | | | |
|---|---|---|---|
| 4,165,748 A | 8/1979 | Johnson | |
| 4,563,177 A | 1/1986 | Kamen | |
| 4,976,700 A | 12/1990 | Tollini | |
| 5,098,399 A | 3/1992 | Tollini | |
| 5,147,322 A | 9/1992 | Bowen et al. | |
| 5,304,146 A * | 4/1994 | Johnson | A61M 25/02 128/DIG. 26 |
| 5,415,642 A | 5/1995 | Shepherd | |
| 5,468,231 A | 11/1995 | Newman et al. | |
| 5,707,703 A | 1/1998 | Rothrum et al. | |
| 5,947,931 A | 9/1999 | Bierman | |

(Continued)

FOREIGN PATENT DOCUMENTS

WO 2011060197 A1 5/2011

*Primary Examiner* — Rebecca E Eisenberg
(74) *Attorney, Agent, or Firm* — Kriegsman & Kriegsman

(57) ABSTRACT

Medical appliance securement device and method of using the same. In one embodiment, the medical appliance securement device includes an anchor. The anchor includes a top surface and a bottom surface. The bottom surface is adhesive. The device also includes a pair of foam blocks secured to the top surface of the anchor and arranged to define a channel for snugly receiving a medical appliance. The device also includes a retaining tab having a first end fixed to the anchor and a second end free to move relative to said anchor and appropriately spaced from the first end of the retaining tab to be wrapped around at least a portion of a medical appliance in the channel. The device also includes a first set of complementary fasteners disposed on the anchor and the retaining tab for detachably coupling the free end of the retaining tab to the anchor.

13 Claims, 21 Drawing Sheets

(56) References Cited

U.S. PATENT DOCUMENTS

| | | |
|---|---|---|
| 5,968,000 A | 10/1999 | Harrison et al. |
| 6,213,979 B1 | 4/2001 | Bierman |
| 6,419,660 B1 | 7/2002 | Russo |
| 6,834,652 B2 | 12/2004 | Altman |
| 7,320,681 B2 | 1/2008 | Gillis et al. |
| D608,887 S | 1/2010 | Kyvik et al. |
| 7,955,307 B2 | 6/2011 | Bierman et al. |
| 8,398,599 B2 | 3/2013 | Bierman |
| 9,233,228 B1 | 1/2016 | LeLievre et al. |
| 2006/0041233 A1 | 2/2006 | Bowen |
| 2006/0247577 A1 | 11/2006 | Wright |
| 2007/0043326 A1 | 2/2007 | Navarro et al. |
| 2008/0065022 A1 | 3/2008 | Kyvik et al. |
| 2008/0294119 A1 | 11/2008 | Schwartz et al. |
| 2009/0299294 A1 | 12/2009 | Pinkus |
| 2009/0326474 A1 | 12/2009 | Bierman |
| 2010/0198161 A1 | 8/2010 | Propp |
| 2011/0077577 A1 | 3/2011 | Sansoucy |
| 2011/0166529 A1 | 7/2011 | LeLievre et al. |
| 2013/0096507 A1 | 4/2013 | LeLievre et al. |
| 2013/0150827 A1* | 6/2013 | Bracken ................ A61M 25/02 604/506 |

\* cited by examiner

MEDICAL APPLIANCE SECUREMENT DEVICE

CROSS-REFERENCE TO RELATED APPLICATIONS

The present application claims the benefit under 35 U.S.C. 119(e) of U.S. Provisional Patent Application No. 62/295,972, filed Feb. 16, 2016, the disclosure of which is incorporated herein by reference.

BACKGROUND OF THE INVENTION

The present invention relates generally to medical appliance securement devices and relates more particularly to a novel medical appliance securement device.

Various medical appliances, or portions thereof, are shaped as generally tubular members. An example of one such medical appliance is a medical catheter. Medical catheters exist for many different applications. One type of medical catheter is a Foley catheter. A Foley catheter is a tubular member that is commonly used to drain urine from a patient. Typically, a Foley catheter is Y-shaped and includes two distinct channels. One of the two channels is open at both ends and is used to conduct urine from the bladder into a collection bag or the like. The other channel has a valve and connects to a balloon, which is used to prevent the catheter from slipping out of the bladder.

There is often a need to secure Foley catheters and other such tubular devices to or near a patient's body so that the devices can appropriately function. For this purpose, medical practitioners and others have often used one or more strips of conventional, medical-grade, adhesive tape to secure a length of the tubular device directly to a patient's skin. However, this method has its shortcomings as the adhesive tape tends to become loose over time. In addition, each time that one wishes to adjust the placement of the medical appliance or each time that one wishes to remove the medical appliance from the patient, the adhesive tape must be removed from the skin of the patient, thereby frequently causing irritation and discomfort to the patient. Moreover, it is important that the catheter be secured to the patient in such a way as to minimize rolling movement of the catheter, particularly when the patient moves.

The following documents, all of which are incorporated herein by reference, may be of interest: U.S. Pat. No. 4,165,748, inventor Johnson, which issued Aug. 28, 1979; U.S. Pat. No. 4,976,700, inventor Tollini, which issued Dec. 11, 1990; U.S. Pat. No. 5,147,322, inventors Bowen et al., which issued Sep. 15, 1992; U.S. Pat. No. 5,304,146, inventors Johnson et al., which issued Apr. 19, 1994; U.S. Pat. No. 6,419,660 B1, inventor Russo, which issued Jul. 16, 2002; U.S. Pat. No. 9,233,228 B1, inventors LeLievre et al., which issued Jan. 12, 2016; U.S. Patent Application Publication No. US 2006/0041233 A1, inventor Bowen, which was published Feb. 23, 2006; U.S. Patent Application Publication No. US 2011/0166529 A1, inventors LeLievre et al., which was published Jul. 7, 2011; and U.S. Patent Application Publication No. US 2013/0096507 A1, inventor LeLievre, which was published Apr. 18, 2013.

SUMMARY OF THE INVENTION

It is an object of the present invention to provide a novel medical appliance securement device.

According to one feature of the invention, the medical appliance securement device of the present invention is relatively inexpensive to make and easy to use.

Therefore, according to one aspect of the invention, there is provided a medical appliance securement device, the medical appliance securing device comprising (a) an anchor, said anchor comprising a top surface and a bottom surface, the bottom surface being adhesive for attachment to a surface; (b) a pair of foam blocks, the foam blocks being secured to the top surface of the anchor and being arranged to define a channel for snugly receiving a medical appliance; (c) a first retaining tab, the first retaining tab having a first end and a second end, the first end of the first retaining tab being fixed to the anchor, the second end of the first retaining tab being free to move relative to said anchor and being appropriately spaced from the first end of the first retaining tab to be wrapped around at least a portion of a medical appliance situated in the channel; and (d) a first set of complementary fasteners, the first set of complementary fasteners being disposed on the anchor and the first retaining tab for detachably coupling the free end of the first retaining tab to the anchor.

In another, more detailed aspect of the invention, the fixed end of the first retaining tab may be disposed in the channel defined by the pair of foam blocks.

In another, more detailed aspect of the invention, the first set of complementary fasteners may comprise complementary hook and loop fasteners.

In another, more detailed aspect of the invention, at least one peelable liner may cover the bottom surface of the anchor.

In another, more detailed aspect of the invention, the anchor and the first retaining tab may be formed from a single sheet of material.

In another, more detailed aspect of the invention, the single sheet of material may be a multi-layer structure comprising a breathable fabric, a pressure-sensitive adhesive adhered to one surface of the breathable fabric, and a water-barrier layer adhered to an opposite surface of the breathable fabric.

In another, more detailed aspect of the invention, the medical appliance securement device may further comprises (a) a second retaining tab, the second retaining tab having a first end and a second end, the first end of the second retaining tab being fixed to the anchor, the second end of the second retaining tab being free to move relative to said anchor and being appropriately spaced from the first end of the second retaining tab to be wrapped around at least a portion of a medical appliance situated in the channel; and (b) a second set of complementary fasteners, the second set of complementary fasteners being disposed on the anchor and the second retaining tab for detachably coupling the free end of the second retaining tab to the anchor.

In another, more detailed aspect of the invention, the fixed end of the second retaining tab may be disposed in the channel defined by the pair of foam blocks.

In another, more detailed aspect of the invention, the first retaining tab and the second retaining tab may jointly define a keyhole-shaped space therebetween.

In another, more detailed aspect of the invention, the second set of complementary fasteners may comprise hook and loop fasteners.

In another, more detailed aspect of the invention, the anchor may comprise a pair of patches, each of the patches having an inner edge, and each of the first retaining tab and the second retaining tab may extend from and interconnects the inner edges of the pair of patches.

In another, more detailed aspect of the invention, the anchor may comprise a pair of patches, each of the patches having an inner edge, and the first retaining tab may extend from and interconnect the inner edges of the pair of patches.

The present invention is also directed at methods of using the above-described medical appliance securing devices.

According to one aspect of the invention, there is provided a method of securing a medical appliance to a patient, the method comprising the steps of (a) providing the medical appliance securement device of claim 1; (b) adhering the bottom surface of the anchor to the patient; (c) aligning a medical appliance within the channel; (d) wrapping at least a portion of the first retaining tab around the medical appliance; and (e) fastening the free end of the first retaining tab to the anchor.

In another, more detailed aspect of the invention, the medical appliance may be a Foley catheter.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF THE INVENTION

Figure 1A:
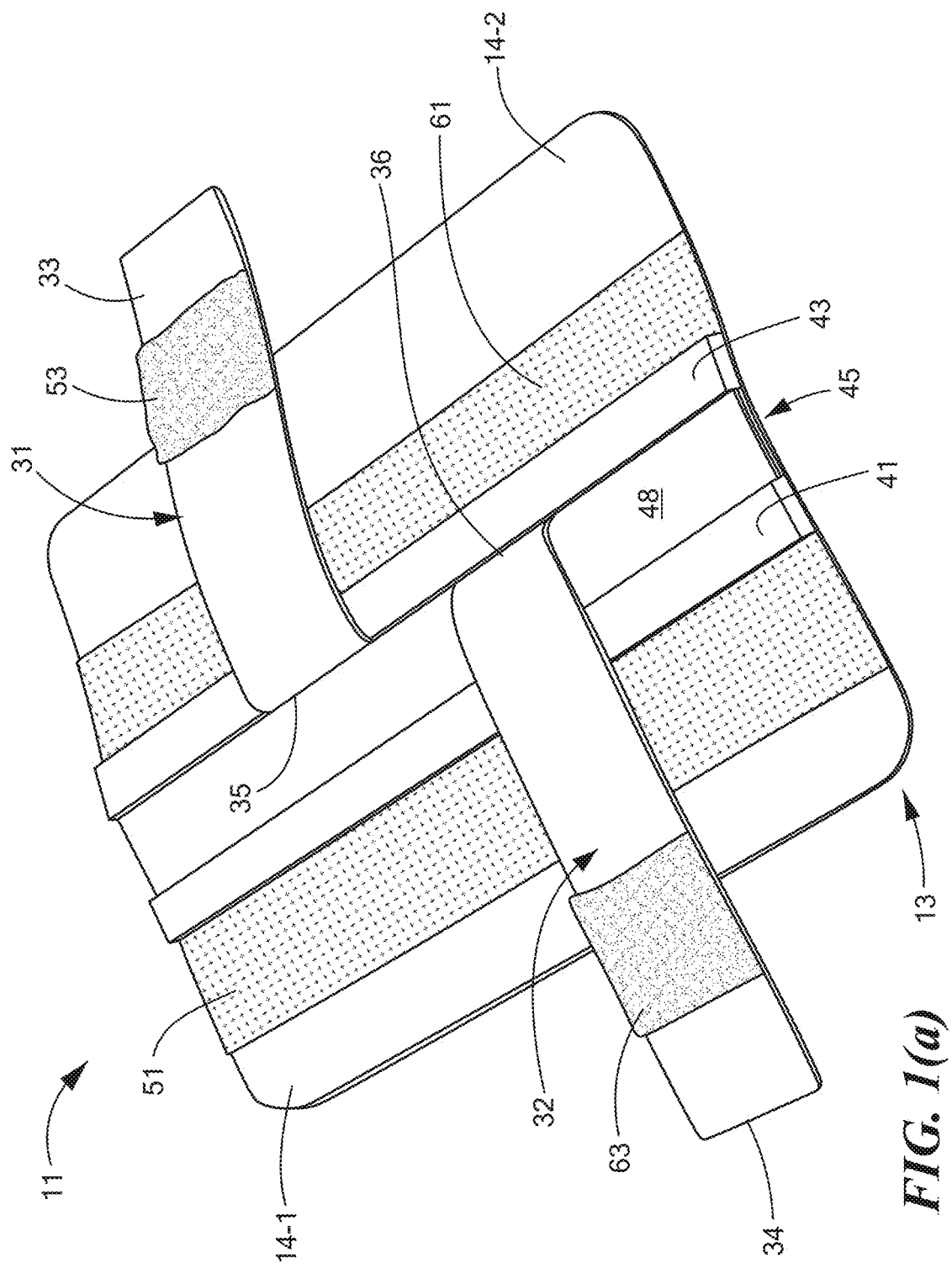
FIGS. 1(a) and 1(b) are perspective and side views, respectively, of a first embodiment of a medical appliance securement device constructed according to the present invention.
Figure 1B:
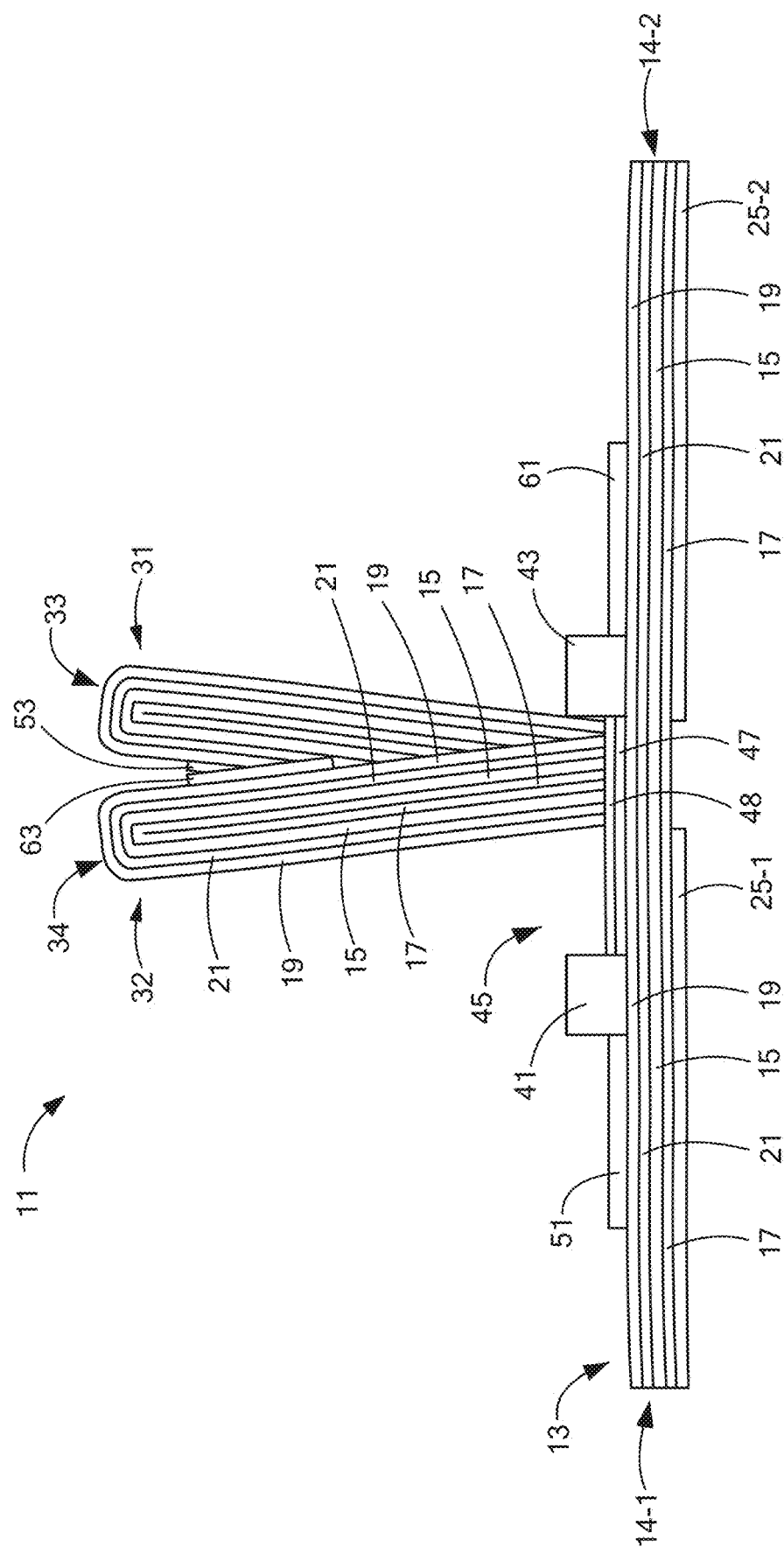
Figure 2A:
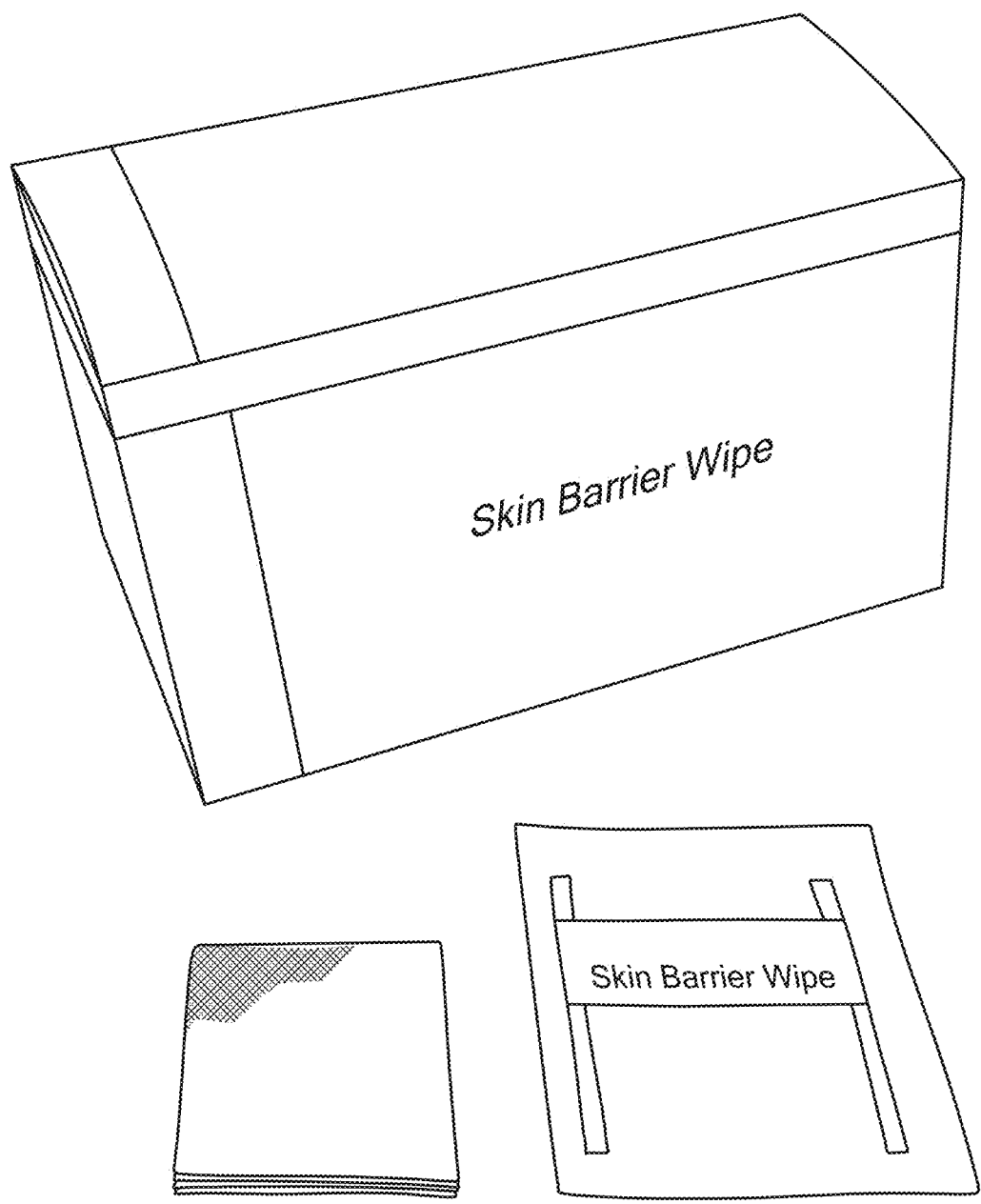
FIGS. 2(a) through 2(f) are perspective views, showing one manner of using the medical appliance securement device of FIGS. 1(a) and 1(b) to secure a Foley catheter.
Figure 2B:
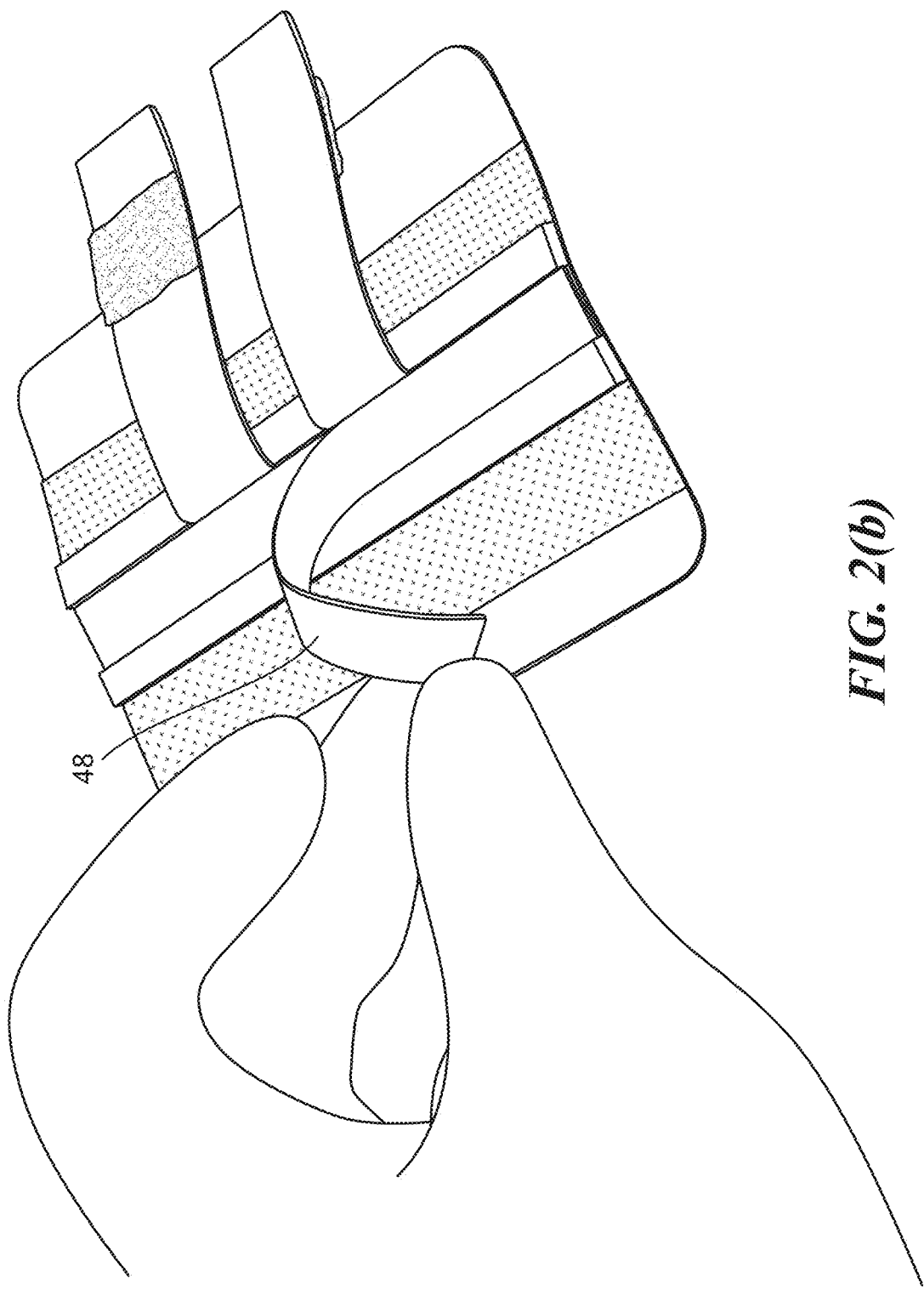
Figure 2C:
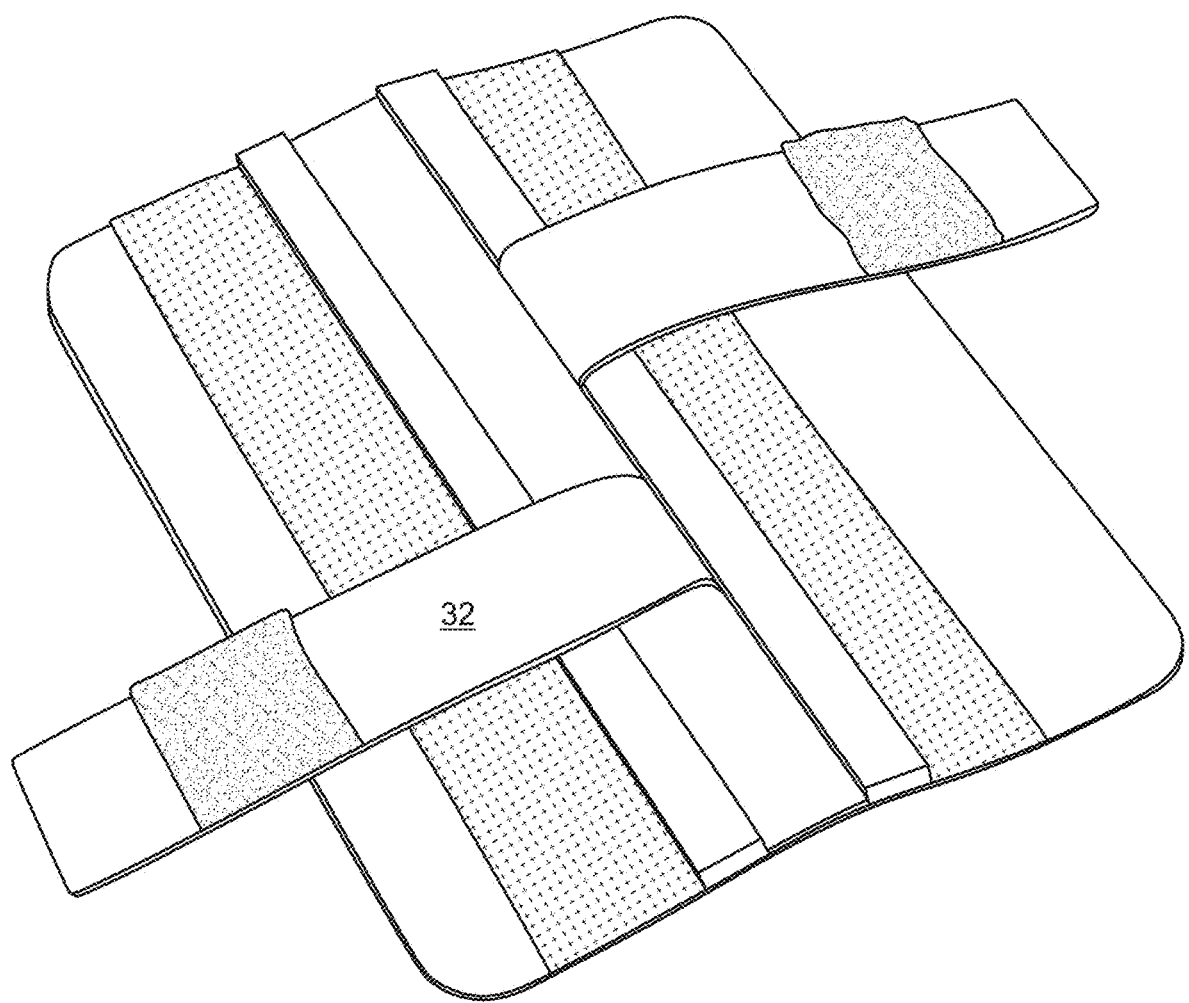
Figure 2D:
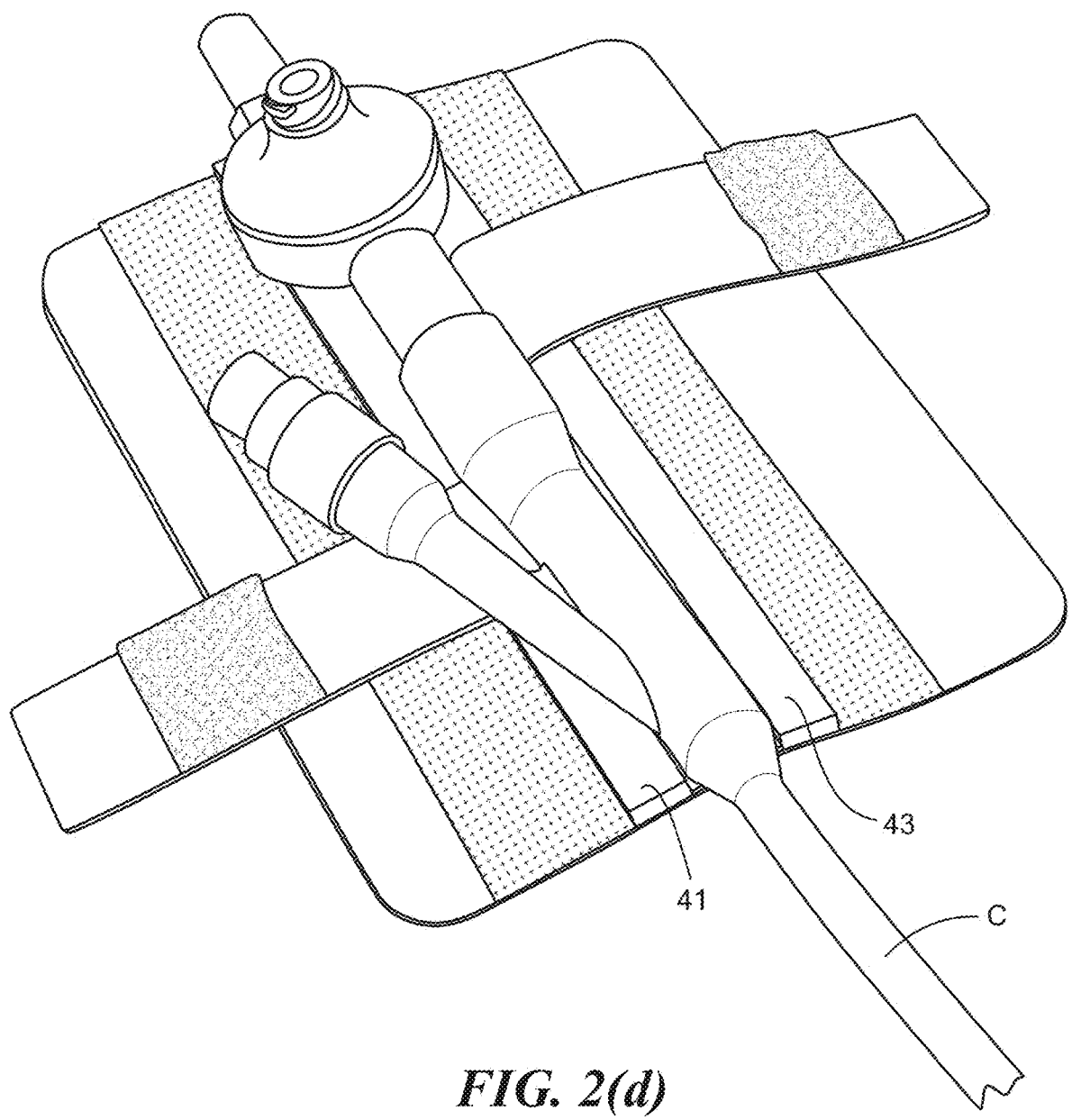
Figure 2E:
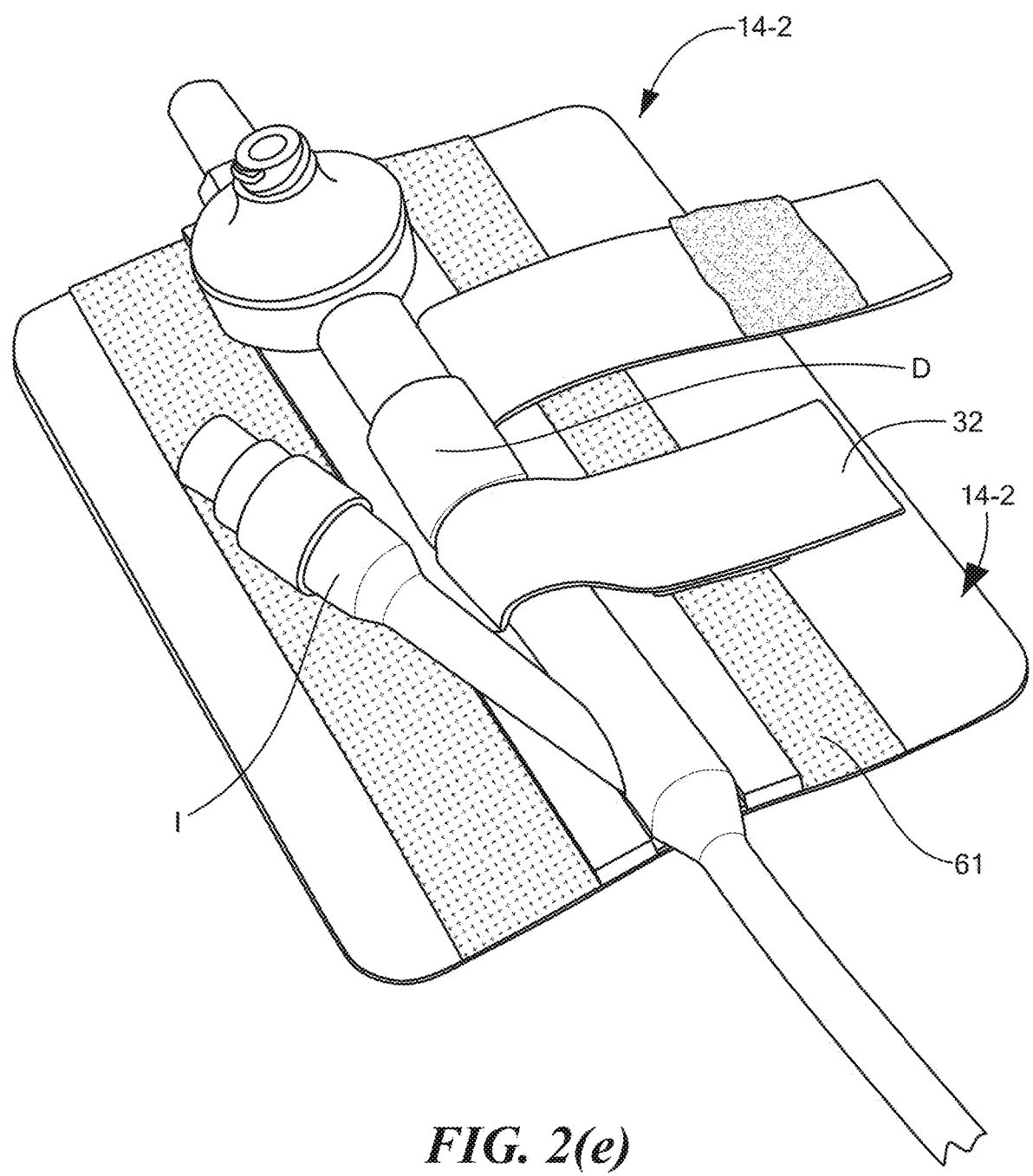
Figure 2F:
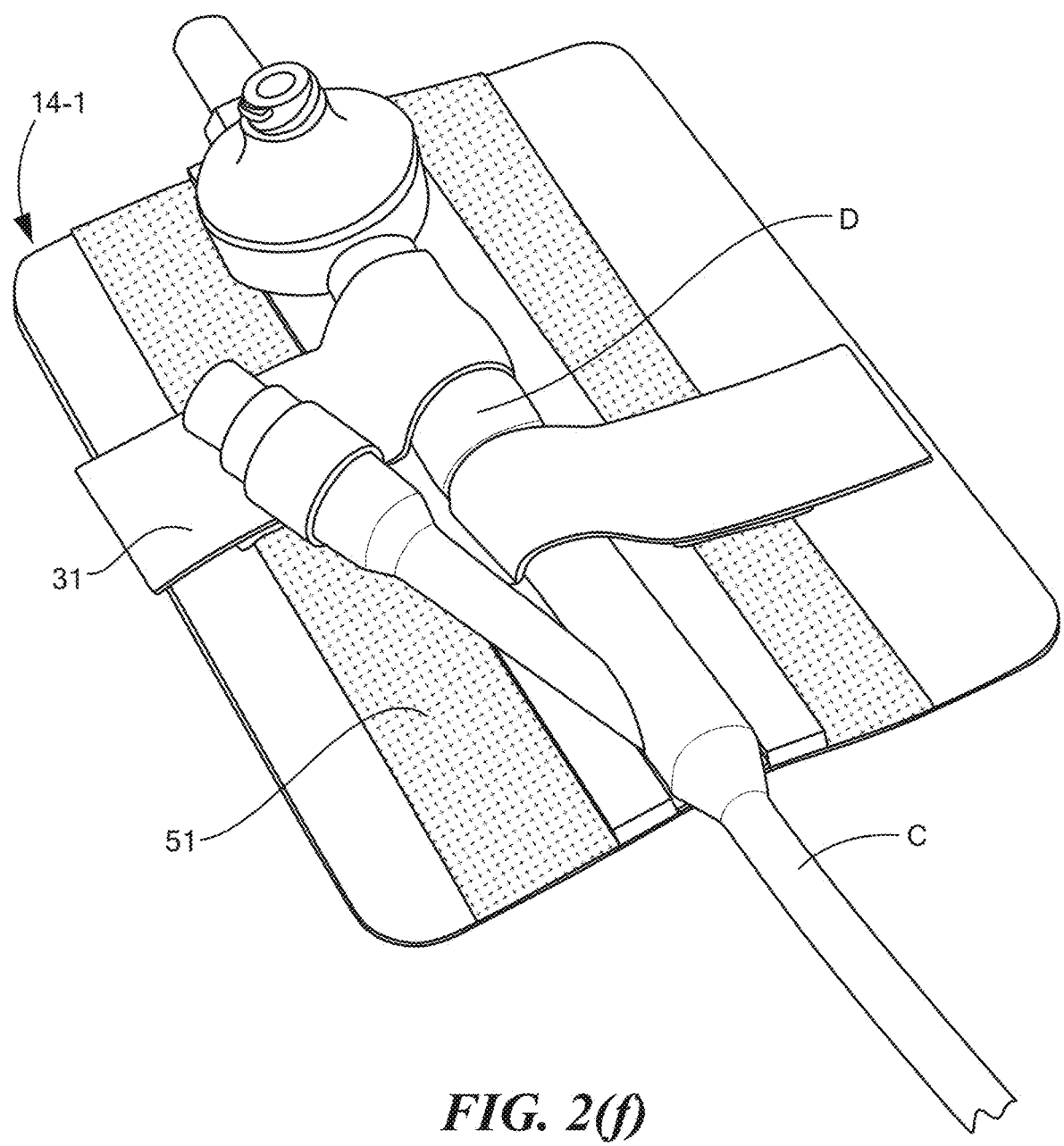

Referring now to FIGS. 1(a) and 1(b), there are shown perspective and side views, respectively, of a first embodiment of a medical appliance securement device constructed according to the present invention, the medical appliance securement device being represented generally by reference numeral 11. (It is to be noted that, in FIG. 1(b), certain structures are not shown to scale.)

Device 11 may comprise an anchor 13. Anchor 13, in turn, may comprise a pair of patches 14-1 and 14-2. Each of patches 14-1 and 14-2 may be a multi-layered structure that may include a base layer 15, an adhesive layer 17, and a moisture barrier layer 19. Base layer 15 may be a layer of breathable fabric and may include, for example, a layer of SONTARA® non-woven, spun-laced, hydro-entangled, polyester fabric having a basis weight of about 1.2 oz/yd$^2$ (E.I. du Pont de Nemours and Company, Wilmington, Del.). Adhesive layer 17, which may be applied directly to the bottom surface of base layer 15, may comprise a pressure-sensitive adhesive and may be, for example, an acrylic pressure-sensitive adhesive having a thickness of about 0.001 inch. Barrier layer 19, which may be positioned over the top surface of base material 15 and may be adhered thereto using a tie layer 21, may be a breathable material that also may be water-resistant, i.e., possesses a high moisture vapor transmission rate (MVTR). For example, barrier layer 19 may be a layer of monolithic polyurethane having a thickness of about 0.001 inch. The aforementioned monolithic polyurethane may be, for example, a non-foamed, caromatiac polyether type having a Shore hardness A of 83; a specific gravity of 1.13; a 100% module-less of 1100; a 300% module-less of 2700; an ultimate tensile of 9000 (elasticity); and a tear resistance of 625.

As noted above, tie layer 21 may serve to adhere barrier layer 19 to base layer 15. Accordingly, where barrier layer 19 is a layer of monolithic polyurethane of the type described above and where base layer 15 includes a layer of SONTARA® non-woven, spun-laced polyester fabric, tie layer 21 may be, for example, an acrylic adhesive having a thickness of about 0.0005 inch.

An example of a multi-layered material suitable for use in forming patches 14-1 and 14-2 is commercially available from DermaMed Coatings Company, LLC (Tallmadge, Ohio) as DM-6001 tape. DM-6001 tape includes a base layer of SONTARA® non-woven, spun-laced, hydro-entangled, polyester fabric having a basis weight of about 1.2 oz/yd$^2$, an acrylic pressure-sensitive adhesive layer having a thickness of about 0.001 inch applied directly to the bottom surface of the base layer, an acrylic adhesive tie layer having a thickness of about 0.0005 inch applied directly to the top surface of the base layer, and a monolithic polyurethane barrier layer having a thickness of about 0.001 inch applied directly to the top surface of the tie layer. A peelable release liner may be removably adhered to the bottom surface of the pressure-sensitive adhesive layer. Using ASTM E96 (an industry standard method for assessing moisture vapor transmission rate), DM-6001 tape has an upright MVTR of 474 grams/m$^2$ over a 24-hour period and an inverted MVTR of 576 grams/m$^2$ over a 24-hour period. Other examples of a multi-layered material suitable for use in forming patches 14-1 and 14-2 are commercially available from DermaMed Coatings Company, LLC (Tallmadge, Ohio) as DM-6004 tape and DM-6005 tape.

Although each of patches 14-1 and 14-2 is generally rectangularly-shaped, it is to be understood that patches 14-1 and 14-2 may be alternatively shaped and may, for example, be arranged relative to one another so as to collectively assume a generally biconcave or butterfly-shape.

Peelable release liners 25-1 and 25-2 may be removably adhered to the bottoms of patches 14-1 and 14-2, respectively. When one wishes to adhere device 11 to a surface, one may peel away liners 25-1 and 25-2, thereby exposing layer 17 of patches 14-1 and 14-2.

Device 11 may further comprise a plurality of flexible retaining tabs 31 and 32, tabs 31 and 32 preferably extending between and interconnecting the inner edges of anchoring patches 14-1 and 14-2. Tabs 31 and 32 and patches 14-1 and 14-2 may constitute a unitary structure, with each of tabs 31 and 32 being formed by doubling onto itself and adhering a narrow bridge of material consisting of the same multi-layered structure used to form patches 14-1 and 14-2. Consequently, each of tabs 31 and 32 may comprise a pair of adhesive layers 17 in direct contact with one another, the adhesive layers being sandwiched between a pair of base layers 15. Base layers 15 and adhesive layers 17 may, in turn, be sandwiched between a pair of tie layers 21, the entire combination of which may be, in turn, sandwiched between a pair of barrier layers 19. Tab 31 may have a free end 33 and a connected end 35, connected end 35 being connected to the inner edges of patches 14-1 and 14-2. In like fashion, tab 32 may have a free end 34 and a connected end 36, connected end 36 being connected to the inner edges of patches 14-1 and 14-2.

Device 11 may further comprise a plurality of blocks 41 and 43. Blocks 41 and 43, which may be generally rectangular prismatic members made of a non-wicking polyurethane foam or similarly suitable material, may be arranged parallel to one another and spaced apart from one another so as to define a generally rectangularly-shaped channel 45 therebetween, channel 45 preferably being suitably dimensioned to snugly receive a Foley catheter or other tubular device therewithin, as well as to receive connected ends 35 and 36 of tabs 31 and 32, respectively. To this end, block 43 may be positioned parallel to and proximate to the inner edge of patch 14-2 (and may be secured to patch 14-2 with a suitable adhesive (not shown) or by other suitable means), and block 41 may be positioned parallel to and spaced a short distance inwardly from the inner edge of patch 14-1 (and may be secured to patch 14-1 with a suitable adhesive (not shown) or by other suitable means). Without wishing to be limited to any particular dimensions, blocks 41 and 43 may have a height, as measured from the top of patches 14-1 and 14-2, of approximately 0.25 inch.

Device 11 may further comprise a strip of double-sided adhesive tape 47. Tape 47, which may be used to adhesively secure a Foley catheter or other medical device within channel 45, may be positioned on top of patch 14-1 between blocks 41 and 43. Tape 47 may be covered with a peelable liner 48. Although not shown, a piece of foam or other cushioning material may be positioned between tape 47 and patch 14-1 to cushion the catheter for patient comfort.

Device 11 may further comprise complementary fasteners on tab 31 and on patch 14-1. For example, such complementary fasteners may comprise a patch of VELCRO® hook fasteners 51 positioned on the top face of patch 14-1 and a patch of VELCRO® loop fasteners 53 positioned on an opposing face of retaining tab 31 proximate to free end 33. Hook fasteners 51 may be secured to patch 14-1 using a suitable adhesive, and loop fasteners 53 may be secured to tab 31 using a suitable adhesive. (As can readily be appreciated, alternatively, VELCRO® hook fasteners 51 may be positioned on retaining tab 31, and VELCRO® loop fasteners 53 may be positioned on patch 14-1.) Other examples of complementary fasteners may comprise snap fasteners, repositionable pressure-sensitive adhesive tapes, and other fastening materials that permit repeated fastening and unfastening. In like fashion, device 11 may also comprise complementary fasteners on tab 32 and on patch 14-2, such complementary fasteners comprising, for example, a patch of VELCRO® hook fasteners 61 positioned on the top face of patch 14-2 and a patch of VELCRO® loop fasteners 63 positioned on an opposing face of retaining tab 32 proximate to free end 35.

Retaining tabs 31 and 32 may be sized and the complementary fasteners on tabs 31 and 32 and patches 14-1 and 14-2 may be appropriately positioned so that tab 31 may be wrapped around at least a portion of the circumference of a desired medical device and then coupled to patch 14-1 and so that tab 32 may be wrapped around at least a portion of the circumference of a desired medical device and then coupled to patch 14-2, whereby the medical device may be secured to device 11. Because tabs 31 and 32 may be wrapped around the medical device in opposite directions, a highly desirable degree of securement may be attained.

Referring now to FIGS. 2(a) through 2(f), there is shown one manner in which device 11 may be used to secure a medical device, such as a medical catheter, particularly a Foley catheter. More specifically, in FIG. 2(a), a skin barrier wipe may be applied to a patient's skin. In step 2(b), peelable liner 48 may be removed. In step 2(c), tab 32 may be crossed over. In step 2(d), the Foley catheter C or other medical device may be placed between blocks 41 and 43. In step 2(e), tab 32 may be moved under the inflation branch I of the Foley catheter C and around the drainage branch D of the catheter C, and the loop fasteners 63 on tab 32 may be secured to the hook fasteners 61 on patch 14-2. In step 2(f), tab 31 may be drawn over the drainage branch D of catheter C, and the loop fasteners 53 on tab 31 may be secured to hook fasteners 51 on patch 14-1.

Figure 3:
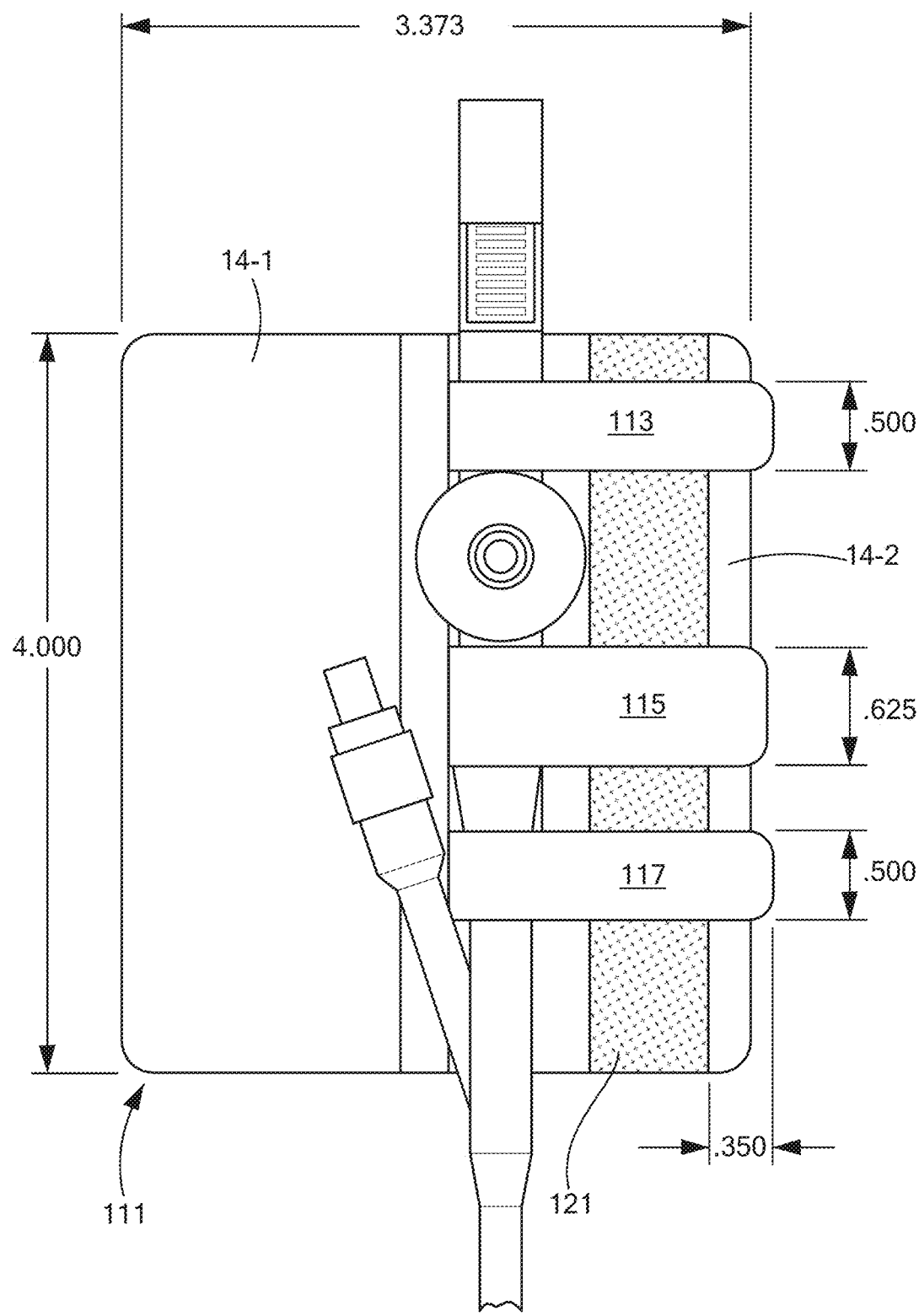
FIG. 3 is a top view of a second embodiment of a medical appliance securement device constructed according to the present invention.
Figure 4A:
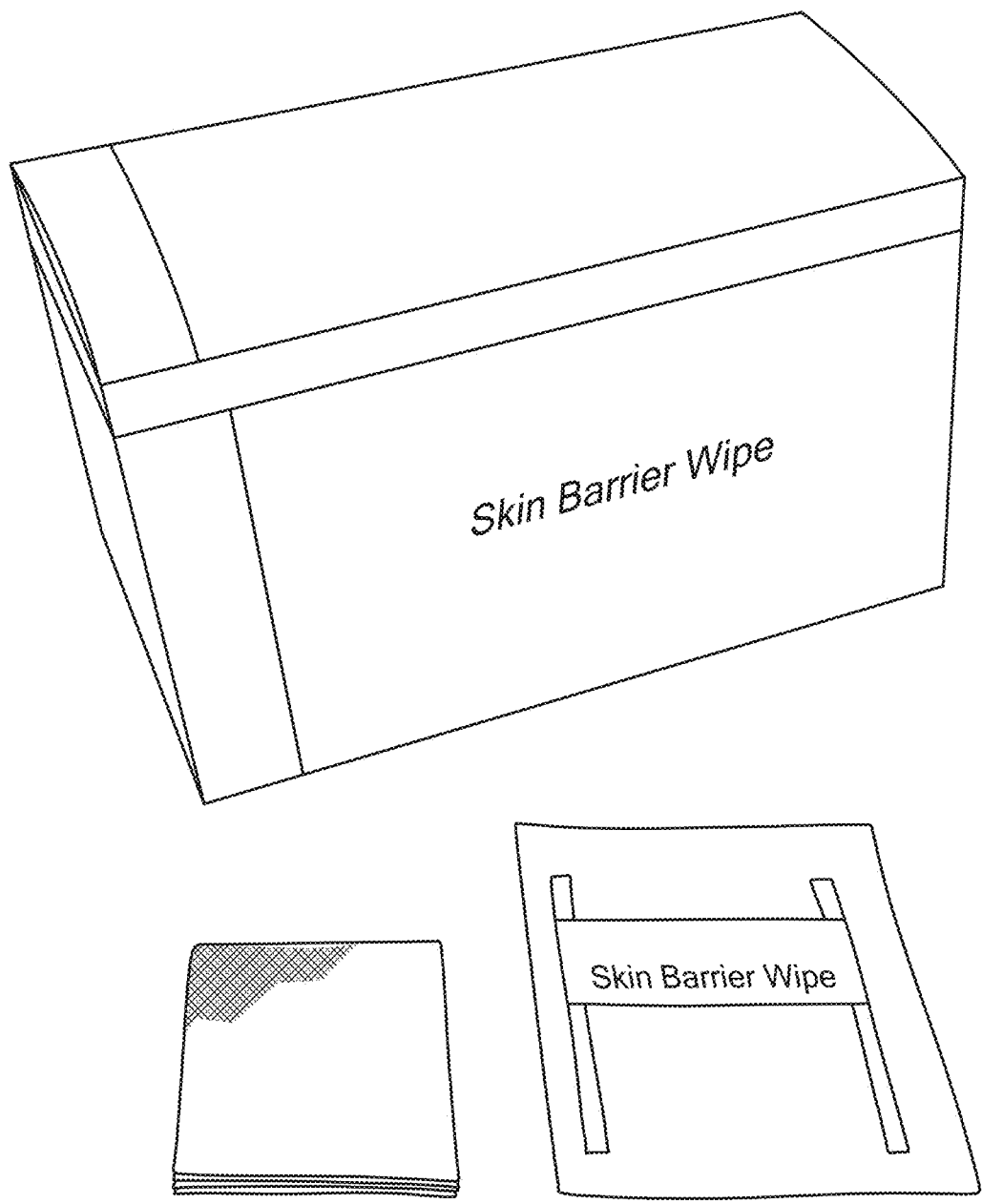
FIGS. 4(a) through 4(e) are perspective views, showing one manner of using the medical appliance securement device of FIG. 3 to secure a Foley catheter.
Figure 4B:
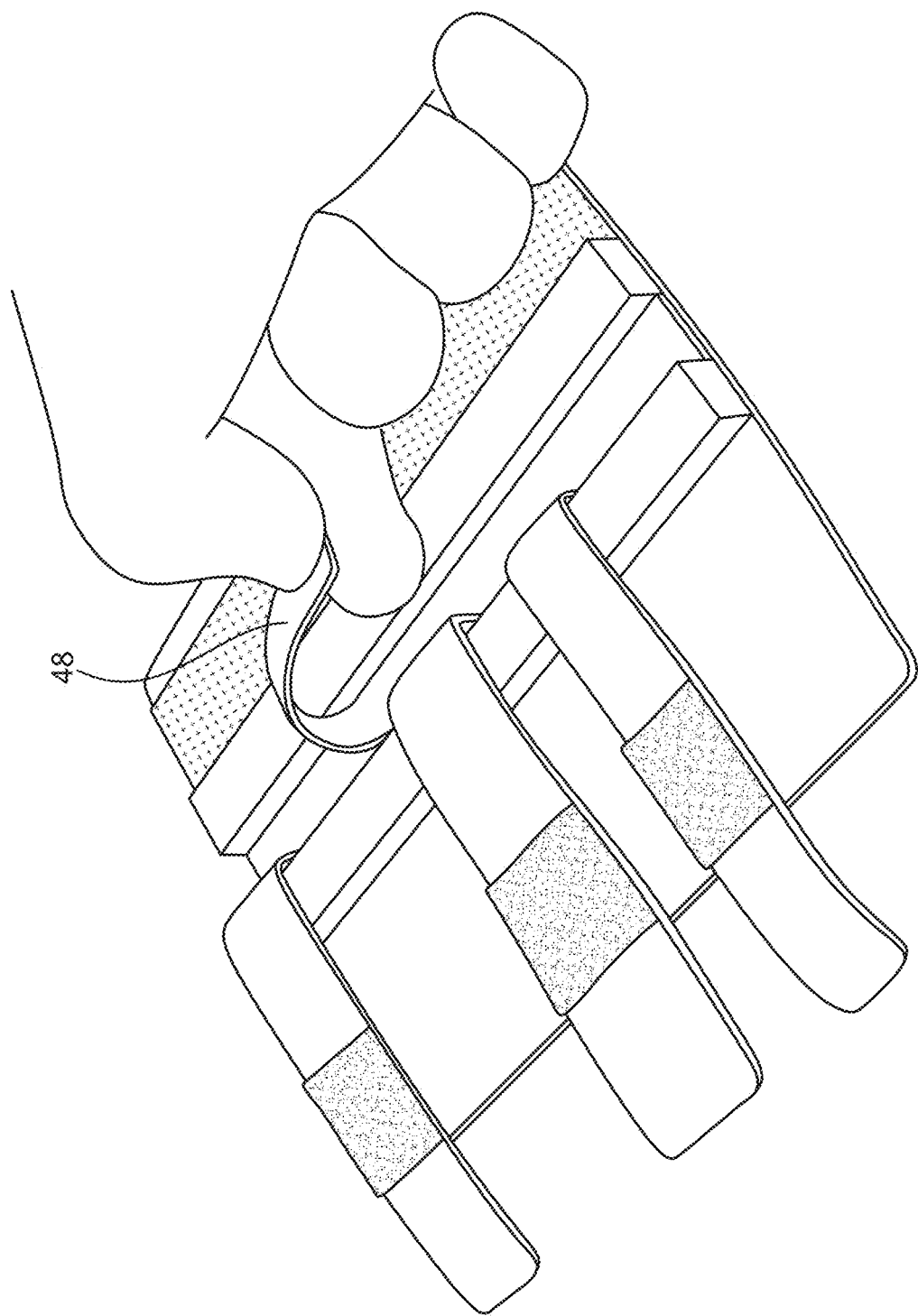
Figure 4C:
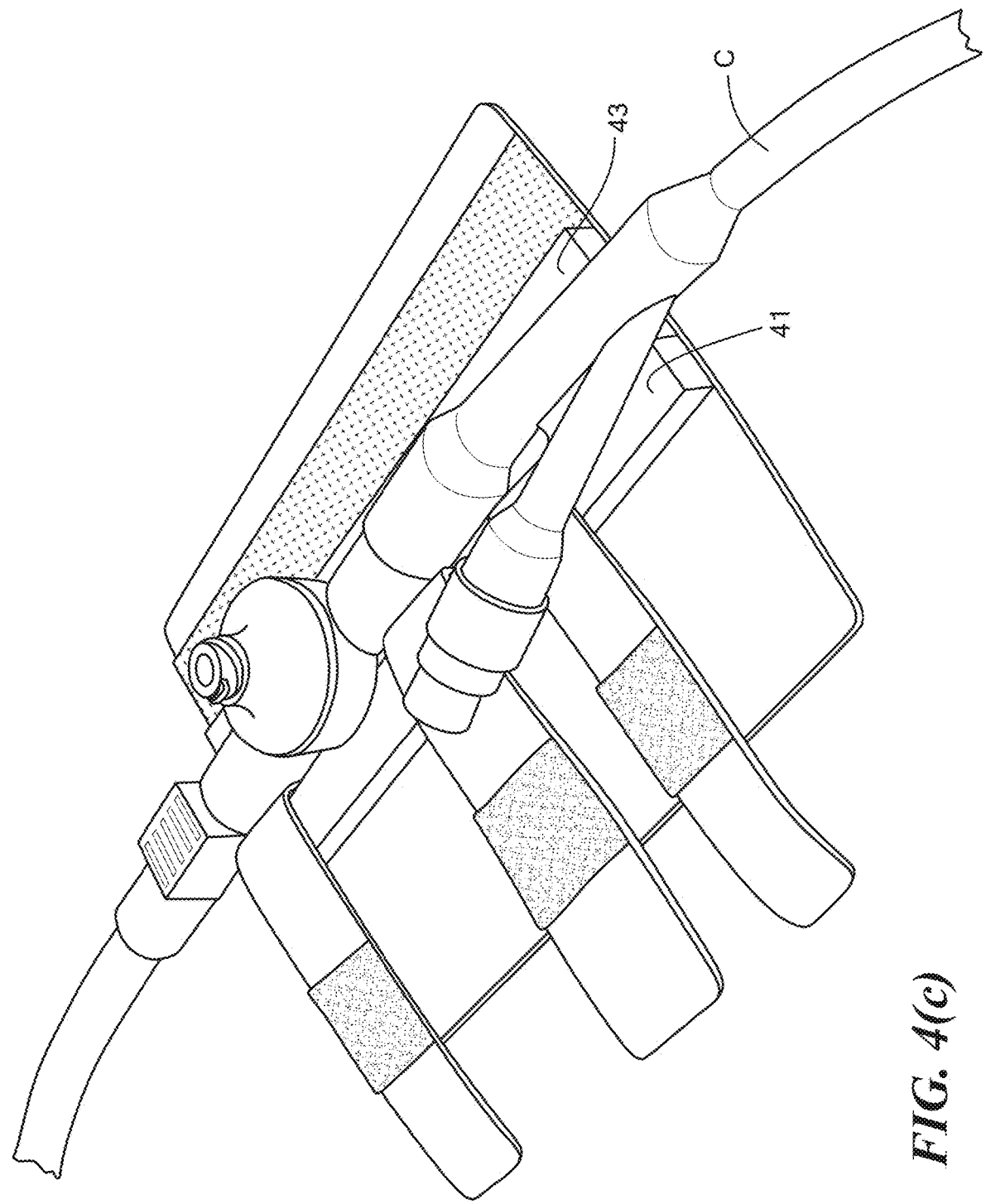
Figure 4D:
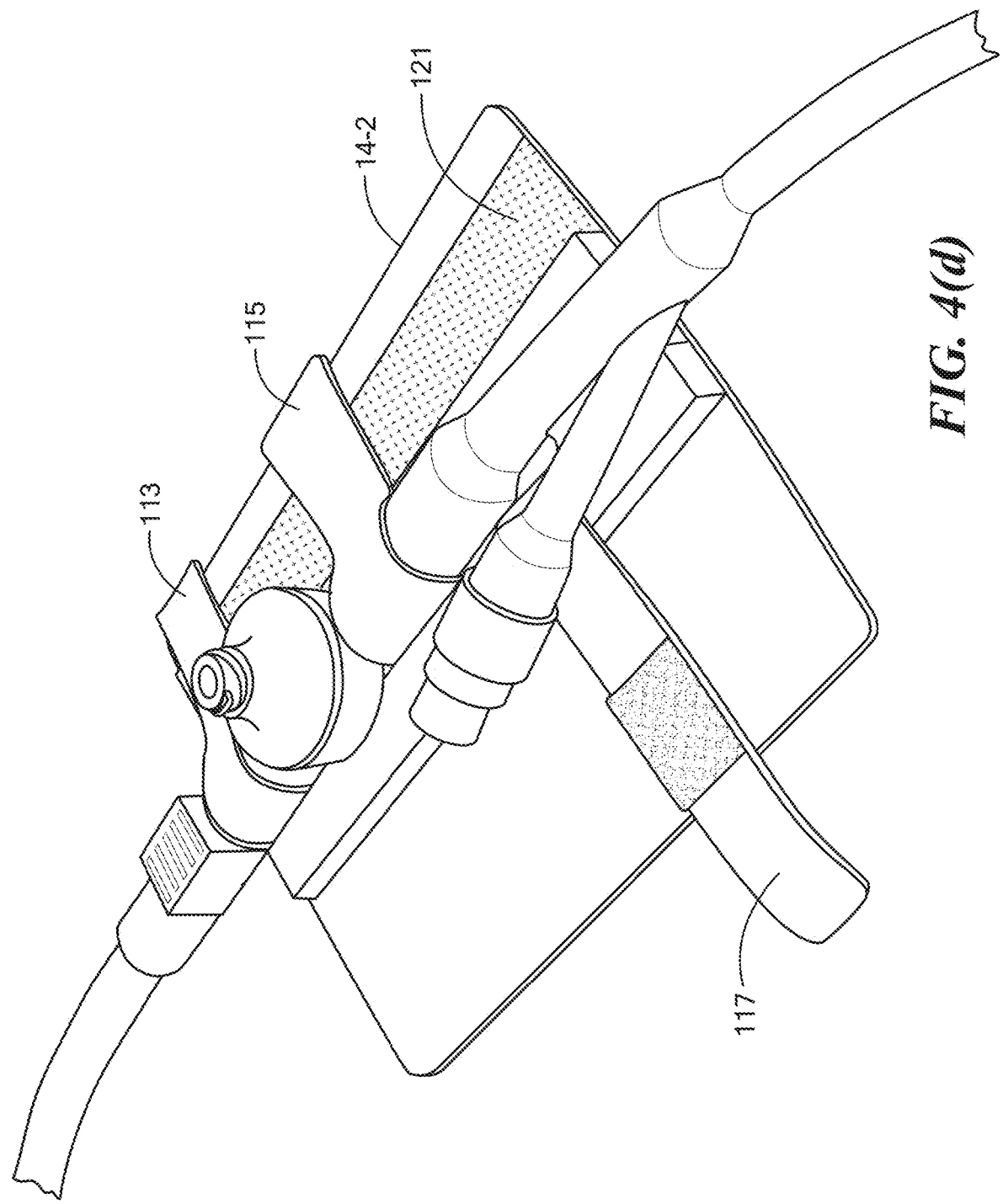
Figure 4E:
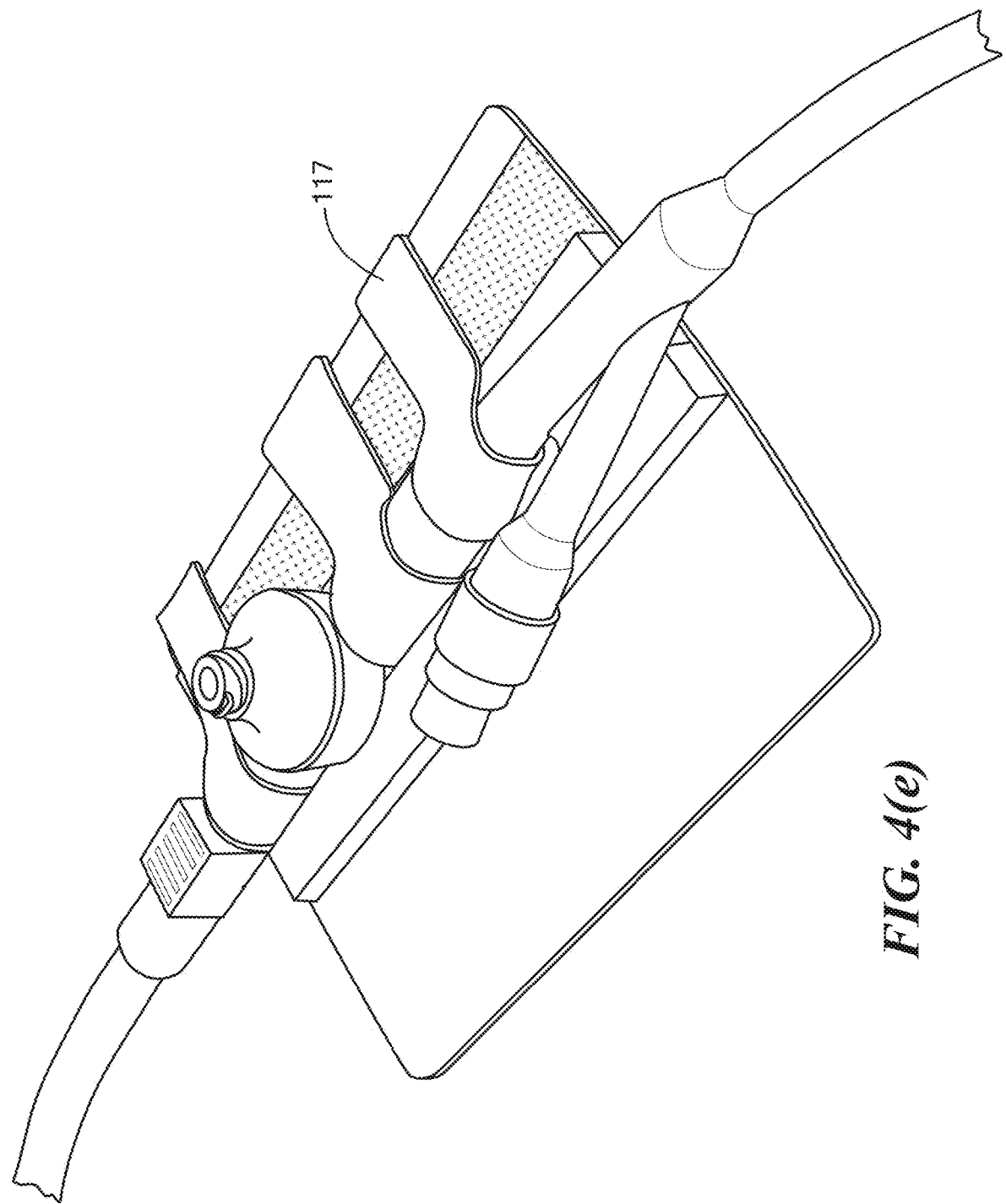

Referring now to FIG. 3, there is shown a top view of a second embodiment of a medical appliance securement device constructed according to the present invention, the medical appliance securement device being represented generally by reference numeral 111.

Device 111 may be similar in many respects to device 11. One difference between devices 111 and 11 may be that, whereas device 11 may comprise two tabs 31 and 32, device 111 may comprise three tabs 113, 115, and 117. Another difference between devices 111 and 11 may be that, whereas device 11 may comprise hook fasteners 51 on patch 14-1 and hook fasteners on patch 14-2 61, device 111 may comprise hook fasteners 121 on patch 14-2 without comprising corresponding hook fasteners on patch 14-1.

Referring now to FIGS. 4(a) through 4(e), there is shown one manner in which device 111 may be used to secure a medical appliance, such as a medical catheter, particularly a Foley catheter. More specifically, in FIG. 4(a), a skin barrier wipe may be applied to a patient's skin. In step 4(b), a peelable liner 48 may be removed. In step 4(c), a Foley catheter C or other medical device may be placed between blocks 41 and 43. In steps 4(*d*) and 4(*e*), tabs 113, 115 and 117 may be secured to hook fasteners 121 on patch 14-2.

Figure 5:
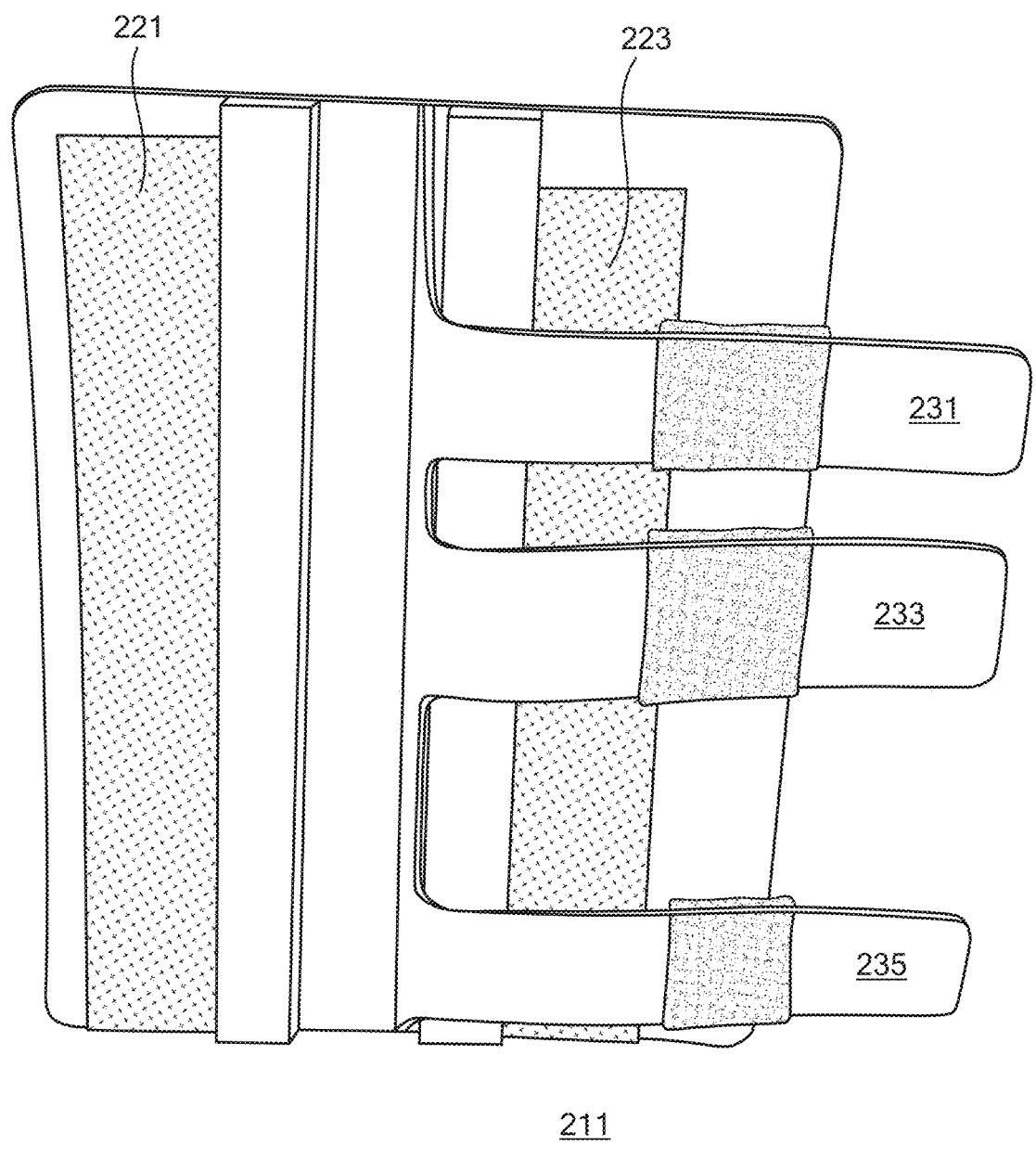
FIG. 5 is a perspective view of a third embodiment of a medical appliance securement device constructed according to the teachings of the present invention.

Referring now to FIG. 5, there is a perspective view of a third embodiment of a medical appliance securement device constructed according to the present invention, the medical appliance securement device being represented generally by reference numeral 211.

Device 211 may be similar in many respects to device 111. One difference between devices 211 and 111 may be that, whereas device 111 may comprise hook fasteners 121 on patch 14-2 without comprising corresponding hook fasteners on patch 14-1, device 211 may comprise hook fasteners 221 on patch 14-1 and hook fasteners 223 patch 14-2. Another difference between devices 211 and 111 may be that, whereas tabs 113, 115 and 117 of device 111 may comprise loop fasteners on only one face thereof, tabs 231, 233 and 235 may comprise loop fasteners on both faces thereof, thereby enabling tabs 231, 233 and 235 to be alternatively secured to hook fasteners 221 and 223.

Figure 6A:
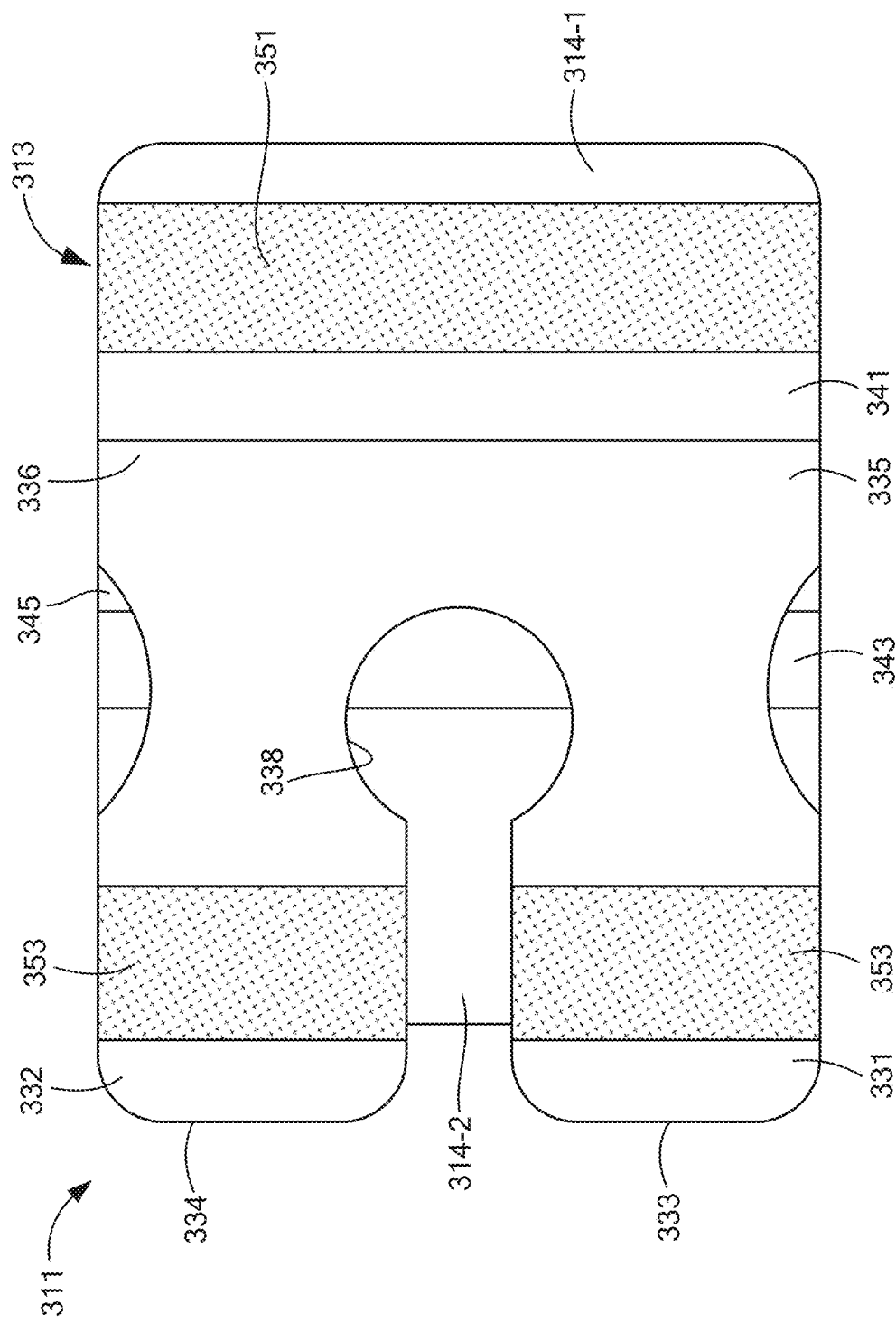
FIGS. 6(a) and 6(b) are top and side views, respectively, of a fourth embodiment of a medical appliance securement device constructed according to the teachings of the present invention.
Figure 6B:
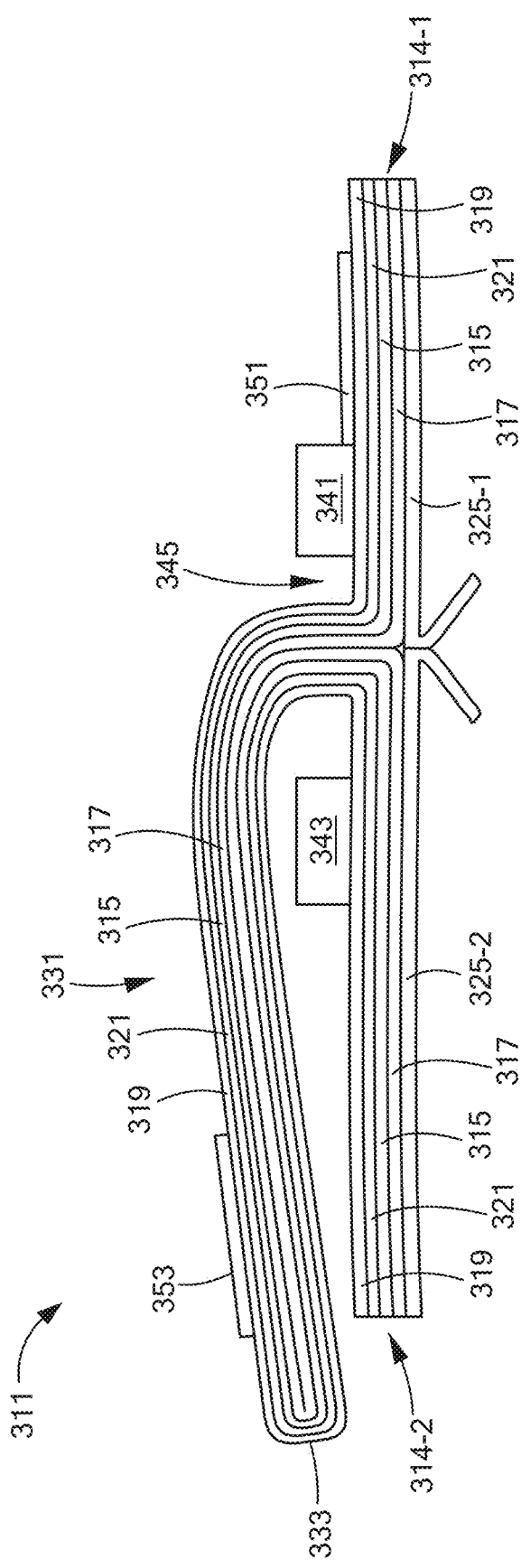
Figure 7A:
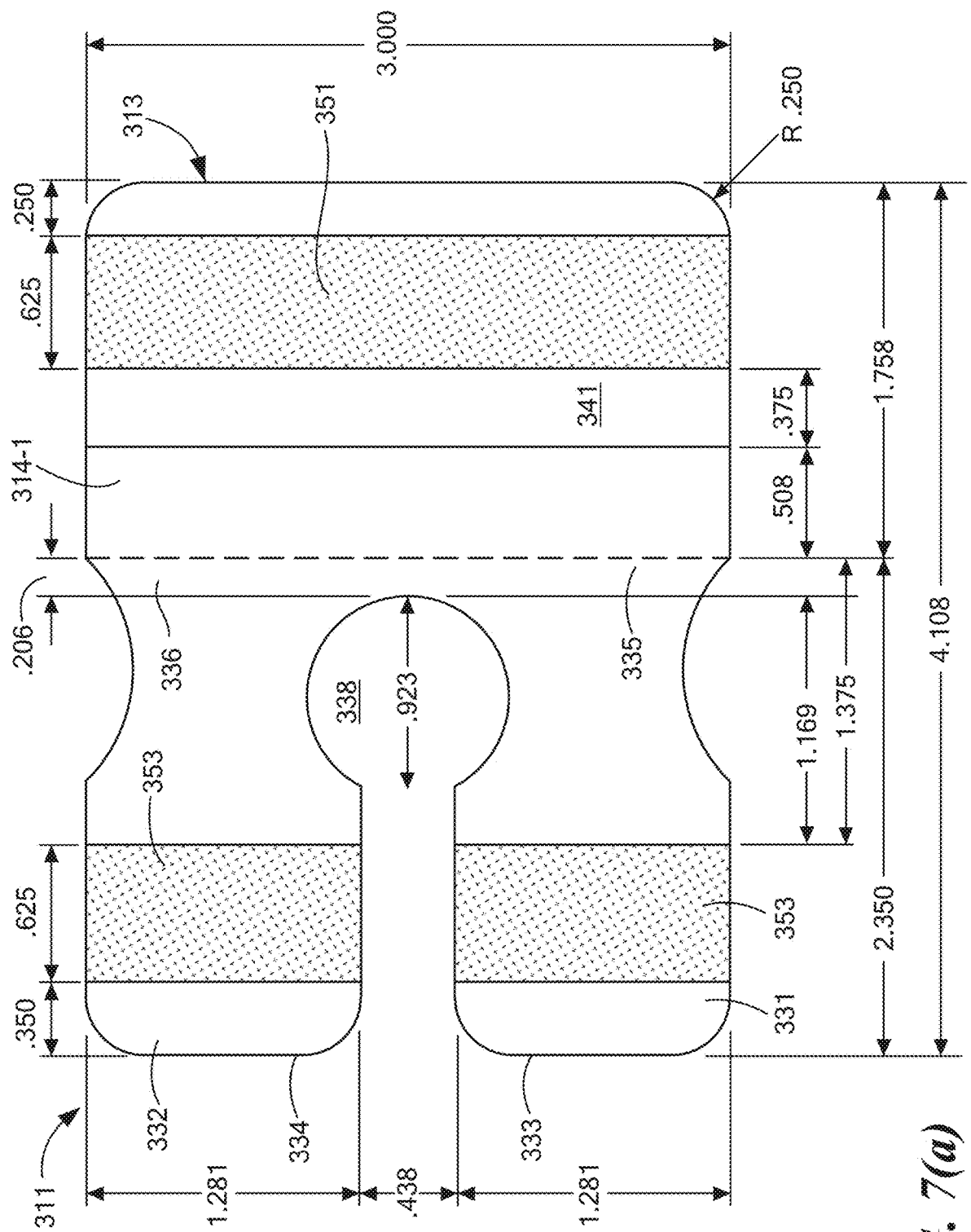
FIGS. 7(a) and 7(b) are top plan and bottom plan views, respectively, of the medical appliance securement device shown in FIGS. 6(a) and 6(b), with the anchor being folded so that one of the patches is positioned under the other patch.
Figure 7B:
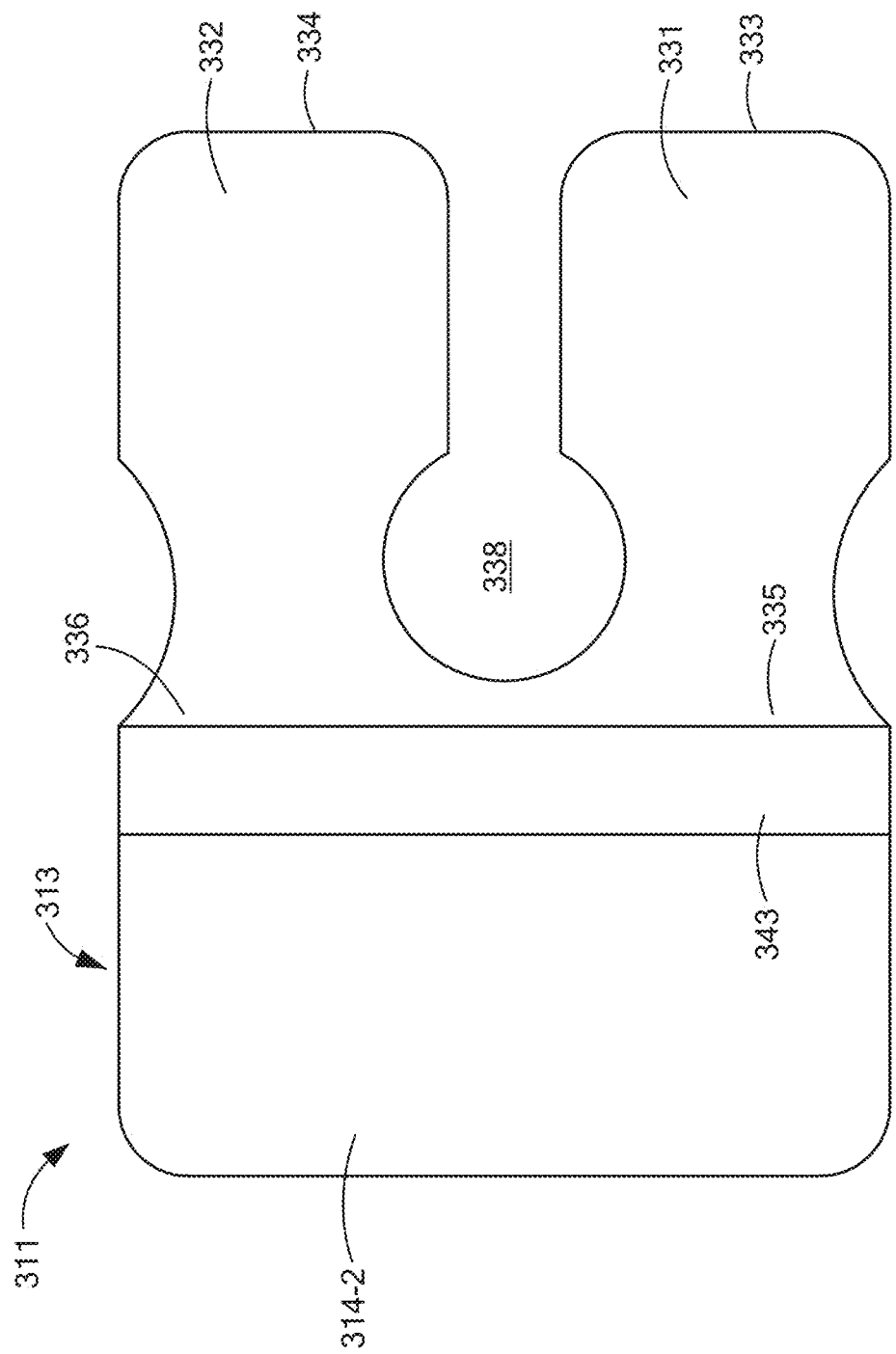

Referring now to FIGS. 6(*a*), 6(*b*), 7(*a*) and 7(*b*), there are shown various views of a fourth embodiment of a medical appliance securement device constructed according to the present invention, the medical appliance securement device being represented generally by reference numeral 311. (It is to be noted that, in FIGS. 6(*a*) and 6(*b*), certain structures are not shown to scale.) Selected exemplary dimensions for device 311 are shown in FIG. 7(*a*).

Device 311 may comprise an anchor 313. Anchor 313, in turn, may comprise a pair of patches 314-1 and 314-2. Each of patches 314-1 and 314-2 may be a multi-layered structure that may include a base layer 315, an adhesive layer 317, a moisture barrier layer 319, and a tie layer 321. Base layer 315, adhesive layer 317, moisture barrier layer 319, and tie layer 321 may be similar in construction and composition to base layer 15, adhesive layer 17, moisture barrier layer 19, and tie layer 21, respectively, of device 11.

An example of a multi-layered material suitable for use in forming patches 314-1 and 314-2 is commercially available from DermaMed Coatings Company, LLC (Tallmadge, Ohio) as DM-6005 tape.

Although each of patches 314-1 and 314-2 is generally rectangularly-shaped, it is to be understood that patches 314-1 and 314-2 may be alternatively shaped and may, for example, be arranged relative to one another so as to collectively assume a generally biconcave or butterfly-shape.

Peelable release liners 325-1 and 325-2 may be removably adhered to the bottoms of patches 314-1 and 314-2, respectively. When one wishes to adhere device 311 to a surface, one may peel away liners 325-1 and 325-2, thereby exposing adhesive layer 317 of patches 314-1 and 314-2.

Device 311 may further comprise a plurality of flexible retaining tabs 331 and 332, tabs 331 and 332 preferably extending between and interconnecting the inner edges of anchoring patches 314-1 and 314-2. Tabs 331 and 332 and patches 314-1 and 314-2 may constitute a unitary structure, with each of tabs 331 and 332 being formed by doubling onto itself and adhering a narrow bridge of material consisting of the same multi-layered structure used to form patches 314-1 and 314-2. Consequently, each of tabs 331 and 332 may comprise a pair of adhesive layers 317 in direct contact with one another, the adhesive layers being sandwiched between a pair of base layers 315. Base layers 315 and adhesive layers 317 may, in turn, be sandwiched between a pair of tie layers 321, the entire combination of which may be, in turn, sandwiched between a pair of barrier layers 319. Tab 331 may have a free end 333 and a connected end 335, connected end 335 being connected to the inner edges of patches 314-1 and 314-2. In like fashion, tab 332 may have a free end 334 and a connected end 336, connected end 336 being connected to the inner edges of patches 314-1 and 314-2. Tabs 331 and 332 may be shaped to jointly define therebetween a keyhole-shaped space 338. As will be seen below, space 338 is particularly well-suited to receive a connection of a Foley catheter.

Device 311 may further comprise a plurality of blocks 341 and 343. Blocks 341 and 343, which may be generally rectangular prismatic members made of a low-density polyethylene foam or similarly suitable material, may be arranged parallel to one another and spaced apart from one another so as to define a generally rectangularly-shaped channel 345 therebetween, channel 345 preferably being suitably dimensioned to snugly receive a Foley catheter or other tubular device therewithin, as well as to receive connected ends 335 and 336 of tabs 331 and 332, respectively. To this end, block 343 may be positioned parallel to and proximate to the inner edge of patch 314-2 (and may be secured to patch 314-2 with a suitable adhesive (not shown) or by other suitable means), and block 341 may be positioned parallel to and spaced a short distance inwardly from the inner edge of patch 314-1 (and may be secured to patch 314-1 with a suitable adhesive (not shown) or by other suitable means). Without wishing to be limited to any particular dimensions, blocks 341 and 343 may have a height, as measured from the top of patches 314-1 and 314-2, of approximately 0.25 inch.

Device 311 may further comprise complementary fasteners on tabs 331 and 332 and on patch 314-1. For example, such complementary fasteners may comprise a patch of VELCRO® hook fasteners 351 positioned on the top face of patch 314-1 and a patch of VELCRO® loop fasteners 353 positioned on an opposing face of each of retaining tabs 331 and 332 proximate to free ends 333 and 334, respectively. Hook fasteners 351 may be secured to patch 314-1 using a suitable adhesive (not shown), and loop fasteners 353 may be secured to tabs 331 and 332 using a suitable adhesive (not shown). (As can readily be appreciated, alternatively, VELCRO® hook fasteners 351 may be positioned on each of retaining tabs 331 and 332, and VELCRO® loop fasteners 353 may be positioned on patch 314-1.) Other examples of complementary fasteners may comprise snap fasteners, repositionable pressure-sensitive adhesive tapes, and other fastening materials that permit repeated fastening and unfastening.

Retaining tabs 331 and 332 may be sized and the complementary fasteners on tabs 331/332 and patch 314-1 may be appropriately positioned so that tabs 331 and 332 may be wrapped around at least a portion of the circumference of a desired medical device and then coupled to patch 314-1, whereby the medical device may be secured to device 311.

Figure 8A:
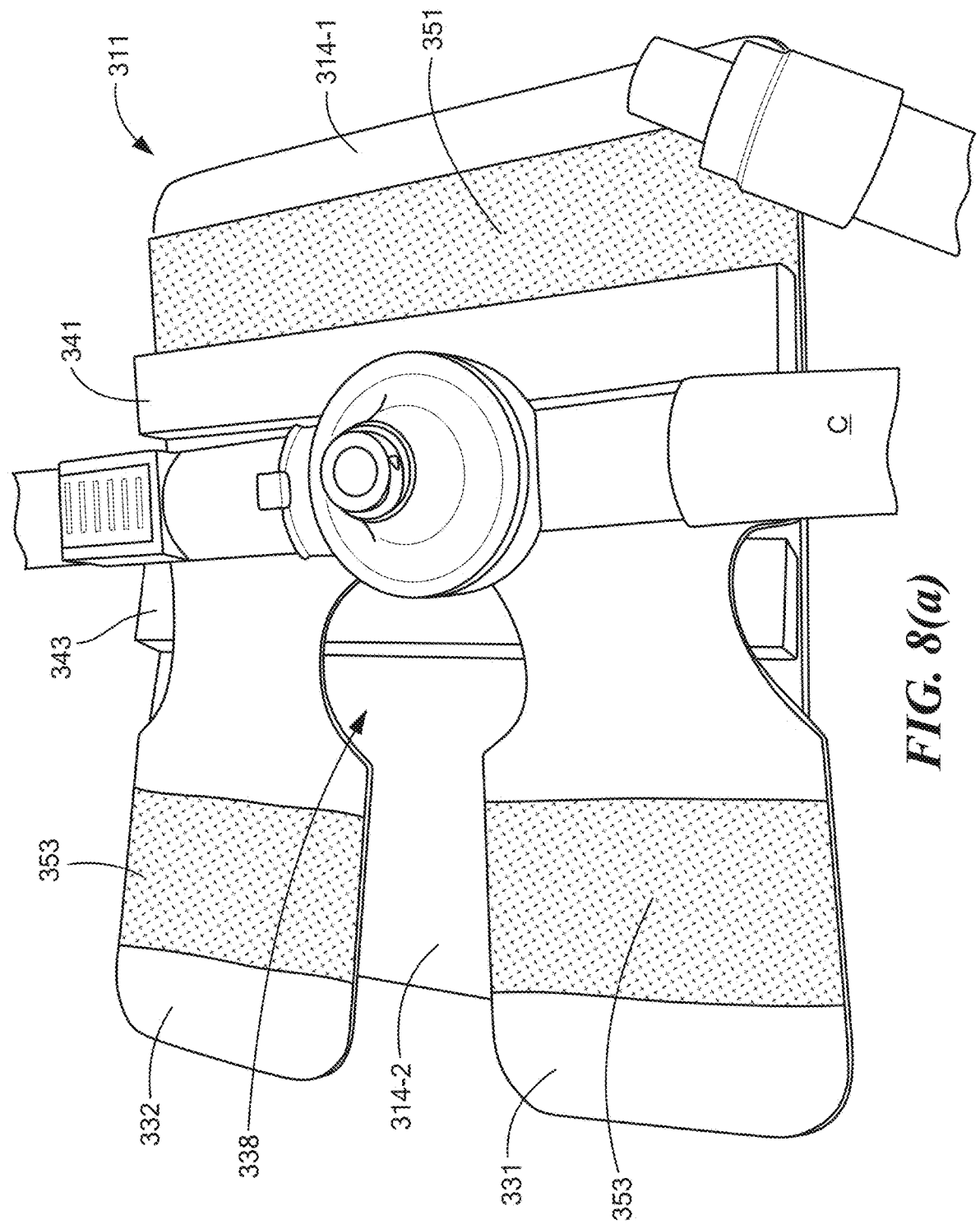
FIGS. 8(a) and 8(b) are perspective views, showing one manner of using the medical appliance securement device of FIGS. 6(a) and 6(b) to secure a Foley catheter.
Figure 8B:
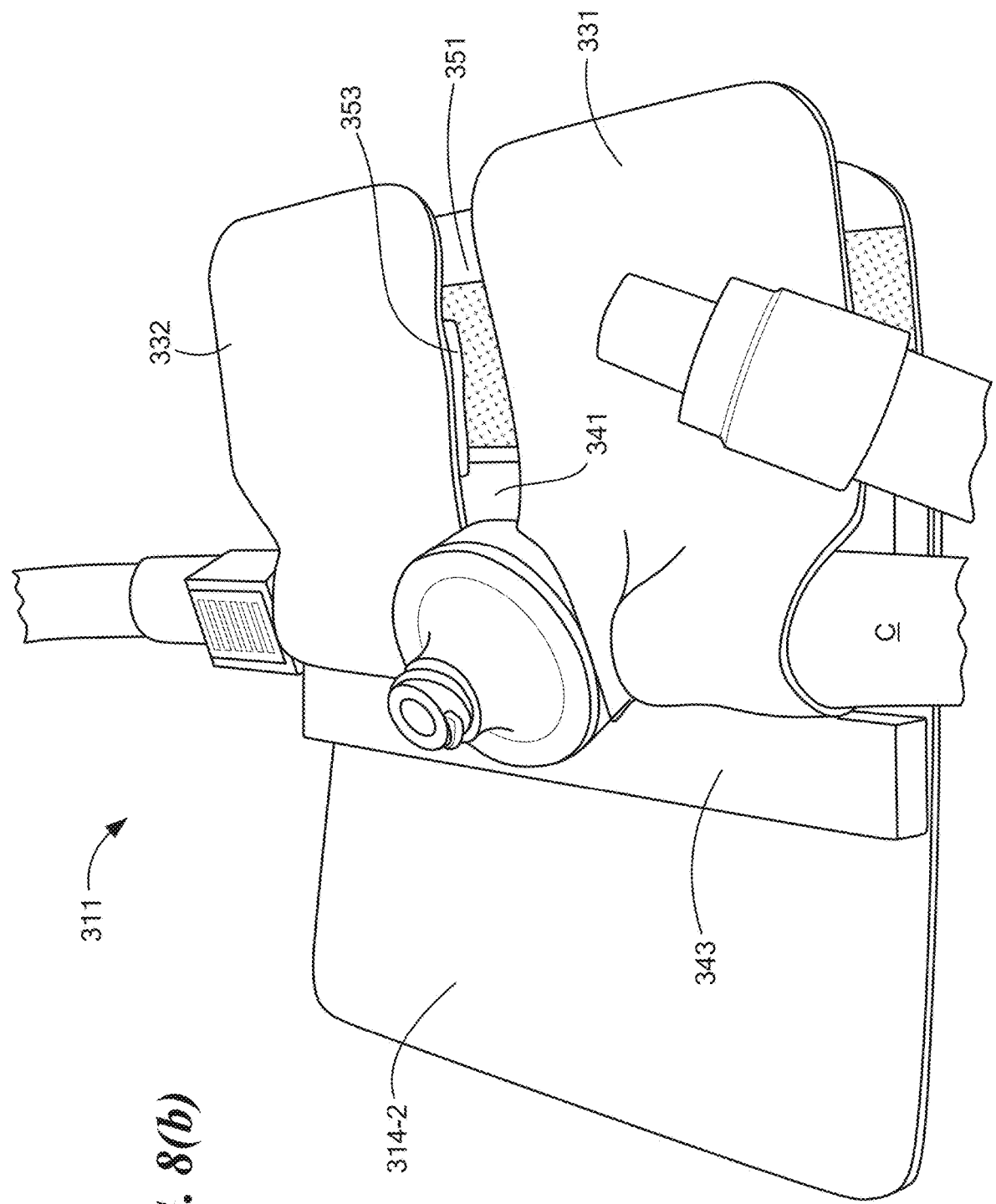

In use, liners 325-1 and 325-2 may be peeled away from patches 314-1 and 314-2, respectively, and patches 314-1 and 314-2 may be adhered to a patient using the thus-exposed adhesive layer 317. As seen best in FIG. 8(*a*), with tabs 331 and 332 positioned over patch 314-2, a medical device, such as a medical catheter, particularly a Foley catheter C, may then be placed between blocks 341 and 343. Then, as seen best in FIG. 8(*b*), tabs 331 and 332 may be moved away from patch 314-2 and around catheter C and then secured to patch 314-1 by mating loop fasteners 353 on tabs 331 and 332 with hook fasteners 351 on patch 314-1.

The embodiments of the present invention described above are intended to be merely exemplary and those skilled in the art shall be able to make numerous variations and modifications to it without departing from the spirit of the present invention. All such variations and modifications are intended to be within the scope of the present invention. For example, although the securement device of the present invention has been discussed herein in the context of being used to secure a Foley catheter, it is to be understood that the securement device of the present invention may be used to secure catheters other than Foley catheters and, in fact, may be used to secure tubular members other than catheters.

What is claimed is:

1. A medical appliance securement device comprising:
   (a) an anchor, said anchor comprising a top surface and a bottom surface, the bottom surface being adhesive for attachment to an attachment surface;
   (b) a pair of foam blocks, the foam blocks being secured to the top surface of the anchor and being arranged to define a channel therebetween for snugly receiving a medical appliance;
   (c) a first retaining tab, the first retaining tab having a first end and a second end, the first end of the first retaining tab being fixed to the top surface of the anchor, the second end of the first retaining tab being free to move relative to said anchor and being appropriately spaced from the first end of the first retaining tab to be wrapped around at least a portion of a medical appliance situated in the channel so that the anchor is positioned between the medical appliance and the attachment surface;
   (d) a first set of complementary fasteners, the first set of complementary fasteners being disposed on the top surface of the anchor and on the first retaining tab for detachably coupling the free end of the first retaining tab to the top surface of the anchor; and
   (e) a peelable liner covering the bottom surface of the anchor;
   (f) wherein the peelable liner and the foam blocks are positioned on opposite sides of the anchor.

2. The medical appliance securement device as claimed in claim 1 wherein the fixed end of the first retaining tab is disposed in the channel defined by the pair of foam blocks.

3. The medical appliance securement device as claimed in claim 1 wherein the first set of complementary fasteners comprise complementary hook and loop fasteners.

4. The medical appliance securement device as claimed in claim 1 wherein the anchor and the first retaining tab are formed from a single sheet of material.

5. The medical appliance securement device as claimed in claim 4 wherein the single sheet of material is a multi-layer structure comprising a breathable fabric, a pressure-sensitive adhesive adhered to one surface of the breathable fabric, and a water-barrier layer adhered to an opposite surface of the breathable fabric.

6. The medical appliance securement device as claimed in claim 1 further comprising
   (g) a second retaining tab, the second retaining tab having a first end and a second end, the first end of the second retaining tab being fixed to the top surface of the anchor, the second end of the second retaining tab being free to move relative to said anchor and being appropriately spaced from the first end of the second retaining tab to be wrapped around at least a portion of a medical appliance situated in the channel; and
   (h) a second set of complementary fasteners, the second set of complementary fasteners being disposed on the top surface of the anchor and on the second retaining tab for detachably coupling the free end of the second retaining tab to the top surface of the anchor.

7. The medical appliance securement device as claimed in claim 6 wherein the fixed end of the second retaining tab is disposed in the channel defined by the pair of foam blocks.

8. The medical appliance securement device as claimed 6 wherein the first retaining tab and the second retaining tab jointly define a keyhole-shaped space therebetween.

9. The medical appliance securement device as claimed in claim 6 wherein the second set of complementary fasteners comprise hook and loop fasteners.

10. The medical appliance securement device as claimed in claim 6 wherein the anchor comprises a pair of patches, each of the patches having an inner edge, and wherein each of the first retaining tab and the second retaining tab extends from and interconnects the inner edges of the pair of patches.

11. The medical appliance securement device as claimed in claim 1 wherein the anchor comprises a pair of patches, each of the patches having an inner edge, and wherein the first retaining tab extends from and interconnects the inner edges of the pair of patches.

12. A method of securing a medical appliance to a patient, the method comprising the steps of:
    (a) providing the medical appliance securement device of claim 1;
    (b) removing the peelable liner from the bottom surface of the anchor;
    (c) adhering the bottom surface of the anchor to the patient;
    (d) positioning a medical appliance on top of the anchor and aligning the medical appliance within the channel;
    (e) wrapping at least a portion of the first retaining tab around the medical appliance; and
    (f) fastening the free end of the first retaining tab to the top surface of the anchor.

13. The method as claimed in claim 12 wherein the medical appliance is a Foley catheter.

* * * * *